US010695002B2

(12) United States Patent
Roh et al.

(10) Patent No.: US 10,695,002 B2
(45) Date of Patent: Jun. 30, 2020

(54) ACTIVITY INFORMATION PROVIDING METHOD AND ELECTRONIC DEVICE SUPPORTING THE SAME

(71) Applicant: Samsung Electronics Co., Ltd., Suwon-si, Gyeonggi-do (KR)

(72) Inventors: Dong Hyun Roh, Yongin-si (KR); Byoung Jip Kim, Suwon-si (KR); Min Hee Jang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 385 days.

(21) Appl. No.: 15/262,784

(22) Filed: Sep. 12, 2016

(65) Prior Publication Data
US 2017/0080288 A1 Mar. 23, 2017

(30) Foreign Application Priority Data

Sep. 22, 2015 (KR) .................. 10-2015-0133746

(51) Int. Cl.
*A61B 5/00* (2006.01)
*G09B 19/00* (2006.01)
(Continued)

(52) U.S. Cl.
CPC .......... *A61B 5/6898* (2013.01); *A61B 5/1118* (2013.01); *A61B 5/1123* (2013.01);
(Continued)

(58) Field of Classification Search
CPC ..... G16H 20/30; A61B 5/1118; A61B 5/6898; G09B 19/003
(Continued)

(56) References Cited

U.S. PATENT DOCUMENTS 5,673,691 A * 10/1997 Abrams ................ G06F 15/025
600/300
6,837,827 B1 * 1/2005 Lee .................... A63B 24/0084
482/8
(Continued)

FOREIGN PATENT DOCUMENTS

KR   10-2010-0102450 A    9/2010
KR   10-2014-0103145 A    8/2014
WO   2014/207294 A1      12/2014

OTHER PUBLICATIONS

European Search Report dated Sep. 6, 2018, issued in European Patent Application No. 16848823.7.

*Primary Examiner* — Thomas J Hong
(74) *Attorney, Agent, or Firm* — Jefferson IP Law, LLP

(57) ABSTRACT

An electronic device and a method for activity information are provided. The electronic device includes a sensor configured to collect sensing information according to a motion of the electronic device, and at least one processor operatively connected with the sensor. The at least one processor is configured to control for obtaining activity information including at least one of an exercise amount that is calculated based on first sensing information obtained according to execution of a specified workout, and a movement amount that is calculated based on second sensing information obtained according to a daily life, determining an expected value of an activity amount, by which a user works out, during a specific time period by a user based on the activity information, and providing guide information for achieving an activity goal associated with the user based on at least one of the expected value of the activity amount and the activity information.

18 Claims, 12 Drawing Sheets

(51) Int. Cl.
  *A61B 5/11* (2006.01)
  *G16H 20/30* (2018.01)
  *A61B 5/024* (2006.01)

(52) U.S. Cl.
  CPC ......... *G09B 19/0038* (2013.01); *G16H 20/30* (2018.01); *A61B 5/0022* (2013.01); *A61B 5/02438* (2013.01); *A61B 2562/0219* (2013.01)

(58) Field of Classification Search
  USPC ....................................................... 434/238
  See application file for complete search history.

(56) References Cited

U.S. PATENT DOCUMENTS

| | | |
|---|---|---|
| 8,475,339 B2 | 7/2013 | Hwang et al. |
| 8,690,578 B1 | 4/2014 | Nusbaum et al. |
| 8,734,296 B1 | 5/2014 | Brumback et al. |
| 8,814,754 B2 | 8/2014 | Weast et al. |
| 8,944,958 B1 | 2/2015 | Brumback et al. |
| 8,954,289 B2 | 2/2015 | Burton et al. |
| 9,017,221 B2 | 4/2015 | Brumback et al. |
| 9,050,488 B2 | 6/2015 | Brumback et al. |
| 9,092,123 B1* | 7/2015 | Kahn .................... G06T 11/203 |
| 9,152,920 B2 | 10/2015 | Bhatia et al. |
| 9,188,460 B2 | 11/2015 | Burton et al. |
| 9,280,640 B2 | 3/2016 | Nusbaum et al. |
| 9,295,413 B2 | 3/2016 | Lee et al. |
| 9,378,657 B1 | 6/2016 | Nusbaum et al. |
| 9,474,955 B2 | 10/2016 | Cobbett et al. |
| 9,539,486 B2 | 1/2017 | Weast et al. |
| 9,757,640 B2 | 9/2017 | Weast et al. |
| 2007/0219059 A1* | 9/2007 | Schwartz ............ A61B 5/0205 482/8 |
| 2010/0075807 A1* | 3/2010 | Hwang ............... G06F 19/3481 482/8 |
| 2011/0087137 A1* | 4/2011 | Hanoun ............... A61B 5/0205 600/587 |
| 2012/0253485 A1* | 10/2012 | Weast .................... G06F 1/163 700/91 |
| 2012/0283855 A1 | 11/2012 | Hoffman et al. |
| 2013/0197680 A1 | 8/2013 | Cobbett et al. |
| 2013/0289744 A1* | 10/2013 | Bavar ................... G05B 11/01 700/9 |
| 2013/0325404 A1* | 12/2013 | Yuen ...................... G06F 11/00 702/182 |
| 2014/0035761 A1 | 2/2014 | Burton et al. |
| 2014/0172362 A1 | 6/2014 | Burton et al. |
| 2014/0200691 A1 | 7/2014 | Lee et al. |
| 2014/0214446 A1 | 7/2014 | Nusbaum et al. |
| 2014/0279720 A1 | 9/2014 | Bhatia et al. |
| 2014/0379106 A1 | 12/2014 | Weast et al. |
| 2015/0042475 A1* | 2/2015 | White .................... G16H 20/30 340/573.1 |
| 2015/0094831 A1 | 4/2015 | Brumback et al. |
| 2015/0094832 A1 | 4/2015 | Brumback et al. |
| 2015/0120025 A1* | 4/2015 | Wisbey ............... G06F 19/3481 700/91 |
| 2015/0133748 A1* | 5/2015 | Edmonds ............... A61B 5/222 600/301 |
| 2015/0182843 A1* | 7/2015 | Esposito ........... G06K 9/00342 700/91 |
| 2015/0231446 A1 | 8/2015 | Brumback et al. |
| 2015/0245801 A1 | 9/2015 | Brumback et al. |
| 2016/0158602 A1 | 6/2016 | Lee et al. |
| 2016/0171905 A1 | 6/2016 | Nusbaum et al. |
| 2016/0256741 A1 | 9/2016 | Holma et al. |
| 2016/0261528 A1* | 9/2016 | Blahnik ................ A61B 5/681 |
| 2016/0262693 A1* | 9/2016 | Sheon ................ G06F 19/3475 |
| 2016/0270717 A1* | 9/2016 | Luna ..................... G16H 50/20 |
| 2017/0072285 A1 | 3/2017 | Weast et al. |
| 2017/0084195 A1* | 3/2017 | Roberts .............. G09B 19/0092 |
| 2018/0181711 A1* | 6/2018 | Boland .................. G16H 40/67 |

* cited by examiner

ACTIVITY INFORMATION PROVIDING METHOD AND ELECTRONIC DEVICE SUPPORTING THE SAME

CROSS-REFERENCE TO RELATED APPLICATION(S)

This application claims the benefit under 35 U.S.C. § 119(a) of a Korean patent application filed on Sep. 22, 2015 in the Korean Intellectual Property Office and assigned Serial number 10-2015-0133746, the entire disclosure of which is hereby incorporated by reference.

TECHNICAL FIELD

The present disclosure relates to a method of providing activity information.

BACKGROUND

At present, as interest in health increases, health management applications are being highly developed. For example, an application that measures the number of steps (e.g., steps walked), a workout time, a workout distance, calorie consumption, or the like and provides the measured result has been released. In addition, an electronic device in which various kinds of sensors are mounted has been provided to support the execution of the application.

Typically, after an electronic device of the related art measures only a movement amount (e.g., the number of steps) of a specific form or measures only an exercise amount on a specified workout (e.g., a running exercise using a treadmill), it may provide a user with the measured result. Accordingly, it is difficult for the electronic device of the related art to provide information about activities in everyday life. Furthermore, since the electronic device of the related art provides only simple status information such as whether to achieve an exercise goal on the specified workout, it may be restrictive to lead the change in an aggressive action of a user for achieving the goal.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method that provides information about activities in everyday life, which includes a movement amount and an exercise amount, and an electronic device supporting the same.

Another aspect of the present disclosure is to provide an activity information providing method that determines an expected value of an activity amount or the probability that an activity goal is achieved, or the like based on an activity goal and an activity information and provide the determined result, and an electronic device supporting the same.

Another aspect of the present disclosure is to provide an activity information providing method that provides notification that a proper activity based on the expected value of an activity amount and the probability that an activity goal is achieved and an electronic device supporting the same.

In accordance with an aspect of the present disclosure, an electronic device is provided. The electronic device includes a sensor configured to collect sensing information according to a motion of the electronic device, and at least one processor operatively connected with the sensor. The at least one processor is configured to control for obtaining activity information including at least one of an exercise amount that is calculated based on first sensing information obtained according to execution of a specified workout, and a movement amount that is calculated based on second sensing information obtained according to a daily life, determining an expected value of an activity amount, by which a user works out, during a specific time period by a user based on the activity information, and providing guide information for achieving an activity goal associated with the user based on at least one of the expected value of the activity amount and the activity information.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1A:
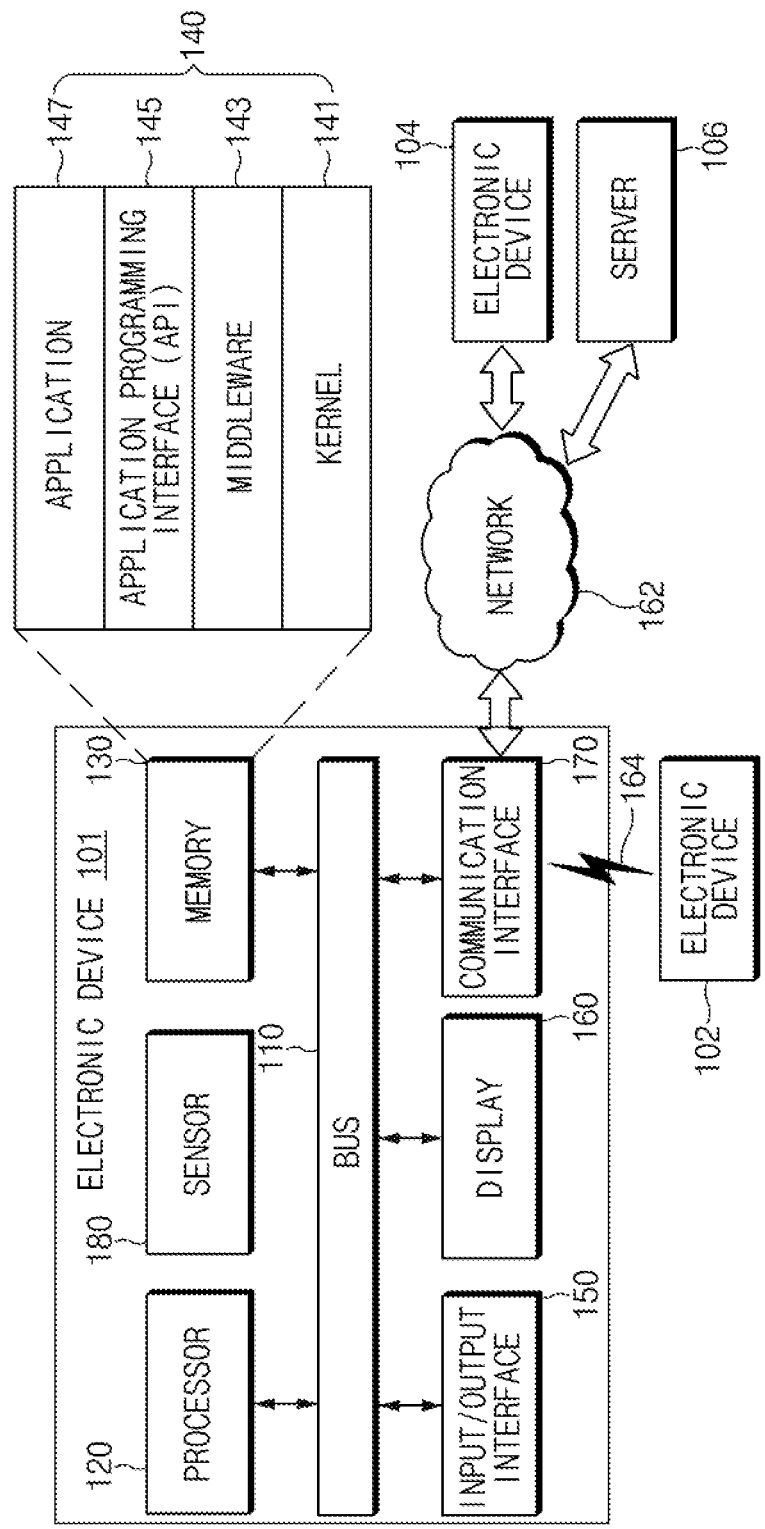
FIG. 1A illustrates an electronic device associated with providing activity information according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The term "include," "comprise," and "have", or "may include," or "may comprise" and "may have" used herein indicates disclosed functions, operations, or existence of elements but does not exclude other functions, operations or elements.

For example, the expressions "A or B," or "at least one of A and/or B" may indicate A and B, A, or B. For instance, the expression "A or B" or "at least one of A and/or B" may indicate (1) at least one A, (2) at least one B, or (3) both at least one A and at least one B.

The terms such as "1st," "2nd," "first," "second," and the like used herein may refer to modifying various different elements of various embodiments of the present disclosure, but are not intended to limit the elements. For instance, "a first user device" and "a second user device" may indicate different users regardless of order or importance. For example, a first component may be referred to as a second component and vice versa without departing from the scope and spirit of the present disclosure.

In various embodiments of the present disclosure, it is intended that when a component (for example, a first component) is referred to as being "operatively or communicatively coupled with/to" or "connected to" another component (for example, a second component), the component may be directly connected to the other component or connected through another component (for example, a third component). In various embodiments of the present disclosure, it is intended that when a component (for example, a first component) is referred to as being "directly connected to" or "directly accessed" another component (for example, a second component), another component (for example, a third component) does not exist between the component (for example, the first component) and the other component (for example, the second component).

The expression "configured to" used in various embodiments of the present disclosure may be interchangeably used with "suitable for," "having the capacity to," "designed to," "adapted to," "made to," or "capable of" according to the situation, for example. The term "configured to" may not necessarily indicate "specifically designed to" in terms of hardware. Instead, the expression "a device configured to" in some situations may indicate that the device and another device or part are "capable of." For example, the expression "a processor configured to perform A, B, and C" may indicate a dedicated processor (for example, an embedded processor) for performing a corresponding operation or a general purpose processor (for example, a central processing unit (CPU) or application processor (AP)) for performing corresponding operations by executing at least one software program stored in a memory device.

Otherwise, all terms used herein may have the same meanings that are generally understood by a person skilled in the art. In general, terms defined in a dictionary should be considered to have the same meanings as the contextual meaning of the related art, and, unless clearly defined herein, should not be understood differently or as having an excessively formal meaning In any case, even the terms defined in the present specification are not intended to be interpreted as excluding embodiments of the present disclosure.

An electronic device according to various embodiments of the present disclosure may include at least one of a smartphone, a tablet personal computer (PC), a mobile phone, a video telephone, an electronic book reader, a desktop PC, a laptop PC, a netbook computer, a workstation, a server, a personal digital assistant (PDA), a portable multimedia player (PMP), a Moving Picture Experts Group phase 1 or phase 2 (MPEG-1 or MPEG-2) audio layer 3 (MP3) player, a mobile medical device, a camera, or a wearable device. The wearable device may include at least one of an accessory-type device (e.g., a watch, a ring, a bracelet, an anklet, a necklace, glasses, a contact lens, a head-mounted device (HMD)), a textile- or clothing-integrated-type device (e.g., an electronic apparel), a body-attached-type device (e.g., a skin pad or a tattoo), or a bio-implantable-type device (e.g., an implantable circuit)

In some various embodiments of the present disclosure, an electronic device may be a home appliance. The smart home appliance may include at least one of, for example, a television (TV), a digital versatile disc (DVD) player, an audio, a refrigerator, an air conditioner, a cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ or PlayStation™), an electronic dictionary, an electronic key, a camcorder, or an electronic picture frame In other various embodiments of the present disclosure, an electronic device may include at least one of various medical devices (e.g., various portable medical measurement devices (e.g., a blood glucose measuring device, a heart rate measuring device, a blood pressure measuring device, a body temperature measuring device, or the like), a magnetic resonance angiography (MRA), a magnetic resonance imaging (MRI), a computed tomography (CT), a scanner, an ultrasonic device, or the like), a navigation device, a global navigation satellite system (GNSS), an event data recorder (EDR), a flight data recorder (FDR), a vehicle infotainment device, electronic equipment for vessels (e.g., a navigation system, a gyrocompass, or the like), avionics, a security device, a head unit for a vehicle, an industrial or home robot, an automatic teller machine (ATM), a point of sales (POS) device of a store, or an internet of things (IoT) device (e.g., a light bulb, various sensors, an electric or gas meter, a sprinkler, a fire alarm, a thermostat, a streetlamp, a toaster, exercise equipment, a hot water tank, a heater, a boiler, or the like).

According to various embodiments of the present disclosure, an electronic device may include at least one of a part of furniture or a building/structure, an electronic board, an electronic signature receiving device, a projector, or a measuring instrument (e.g., a water meter, an electricity meter, a gas meter, a wave meter, or the like). An electronic device may be one or more combinations of the above-mentioned devices. An electronic device according to some various embodiments of the present disclosure may be a flexible device. An electronic device according to an embodiment of the present disclosure is not limited to the above-mentioned devices, and may include new electronic devices with the development of new technology.

Hereinafter, an electronic device according to various embodiments of the present disclosure will be described in more detail with reference to the accompanying drawings. The term "user" used herein may refer to a person who uses an electronic device or may refer to a device (e.g., an artificial intelligence electronic device) that uses an electronic device.

FIG. 1A illustrates an electronic device associated with providing activity information according to various embodiments of the present disclosure.

Referring to FIG. 1A, an electronic device 101 may obtain activity information including an exercise amount that is calculated based on sensing information obtained according to the execution of a specified workout and a movement amount that is calculated based on sensing information obtained according to a daily life. The electronic device 101 may determine the expected value of an activity amount based on the activity information and may provide guide information for achieving an activity goal based on the expected value of an activity amount. The movement amount may include a measured value (e.g., sensing information) on a movement (or a move, a motion, or the like) in a daily life (e.g., commuting, attending school, shopping, or the like) of a user except for a specific time (e.g., a sleep time, a workout time, or the like). Furthermore, the exercise amount may include the measured value (e.g., sensing information) according to a specified workout (e.g., running using a treadmill, swimming, riding a bicycle, or the like). The measured value may include, for example, sensing information according to the motion of the electronic device 101. The electronic device 101 may lead the change in an active action of a user for achieving the activity goal based on the movement amount, the exercise amount, and the like that are obtained from the life pattern of a user. The specified workout may be determined based on a starting phase of the sensing information (e.g., measurement of a sudden increase in heartbeat, along with a related motion of the electronic device 101, may suggest that the user is running).

According to various embodiments, with reference to FIG. 1A, the electronic device 101 may distinguish the movement amount and the exercise amount based on the characteristic of the sensing information. For example, in the case where each of measured values collected through a sensor 180 is greater than or equal to a specific magnitude during a specific time, the electronic device 101 may classify the measured values as the exercise amount. According to various embodiments of the present disclosure, in the case where a part of the measured values collected during the specific time is smaller than the specific magnitude, the electronic device 101 may classify the measured values as the movement amount. According to various embodiments of the present disclosure, the electronic device 101 may distinguish the exercise amount and the movement amount based on whether to perform a workout application (e.g., an application that is capable of providing the measured value according to the execution of an exercise). For example, the electronic device 101 may classify sensing information, which is collected while the workout application is performed, as the exercise amount and may classify sensing information, which is collected while the workout application is not yet performed, as the movement amount. According to various embodiments of the present disclosure, the electronic device 101 may differently assign weight to the movement amount and the exercise amount. For example, compared with the movement amount, the electronic device 101 may assign relatively high weight to the exercise amount. As such, a user may increase a probability that an activity goal is achieved, by executing a specified workout.

The electronic device 101 that provides the activity information may include, referring to FIG. 1A, a bus 110, a processor 120, a memory 130, an input/output interface 150, a display 160, a communication interface 170, and the sensor 180. According to an embodiment, the electronic device 101 may not include at least one of the above-described elements or may further include any other component(s).

The bus 110 may include a circuit for connecting the above-mentioned elements 110, 120, 130, 150, 160, and 170 to each other and transferring communications (e.g., control messages and/or data) among the above-mentioned elements.

The processor 120 may include at least one of a central processing unit (CPU), an application processor (AP), or a communication processor (CP). The processor 120 may perform data processing or an operation related to communication and/or control of at least one of the other elements of the electronic device 101.

According to various embodiments of the present disclosure, the processor 120 may control the sensor 180 included in the electronic device 101. According to various embodiments, the sensor 180 may collect the sensing information (e.g., an execution time, the intensity of execution, or the like) according to an activity (e.g., walking, running, riding a bicycle, or the like) and may send the sensing information to the processor 120. According to various embodiments, the processor 120 may distinguish a kind of activity by analyzing the sensing information and may calculate an activity amount (e.g., an exercise amount or a movement amount) for each kind of activity in a specific manner. Moreover, the processor 120 may calculate additional information, for example, calorie consumption or the like based on the calculated information and may include the calculated additional information in the activity information. According to various embodiments, the sensor 180 may include an acceleration sensor, a gyro sensor, or the like. According to an embodiment, the sensor 180 may include a heartbeat sensor, an illuminance sensor, or the like.

According to various embodiments of the present disclosure, the processor 120 may analyze the pattern of the collected activity information. For example, the processor 120 may analyze an activity pattern during a specific time period (e.g., one day, one week, one month, one year, or the like). Moreover, the processor 120 may calculate the expected value of an activity amount based on the activity information, activity pattern information, and the like. The expected value of an activity amount may include the activity amount, which a user works out by, during a specified time period (e.g., one day). According to various embodiments, the processor 120 may determine a probability that an activity goal is achieved, based on a specified activity goal, the expected value of an activity amount, and the like. The probability that an activity goal is achieved may include information in which a probability that the specified activity goal is achieved during a specified time period is expressed as a value (e.g., a percentage).

According to various embodiments of the present disclosure, the processor 120 may determine a recommended activity based on the expected value of an activity amount and the probability that an activity goal is achieved. According to an embodiment, the processor 120 may calculate a recommended activity amount, by which a user works out to achieve the activity goal, and may determine the recommended activity, which a user executes to achieve the recommended activity amount until a target time, based on the calculated result. In the case where the processor 120 determines the recommended activity, it may use information, for example, a kind of activity, an activity amount per time according to each activity, and the like. In this regard, the processor 120 may collect the information of a kind of activity, an activity amount per time according to each activity, and the like from an external electronic device (e.g., a first external electronic device 102, a second external electronic device 104, or a server 106). In addition, the processor 120 may store information, which is collected from the external electronic device, in the memory 130.

According to various embodiments of the present disclosure, the processor 120 may store the collected activity information, the analyzed activity pattern information, or the like in the memory 130. According to an embodiment, the processor 120 may control the memory 130 to store the activity information, the activity pattern information, or the like together with time information. For example, the processor 120 may sequentially store the activity information in the memory 130 together with the collected time information. Furthermore, the processor 120 may store information about the activity pattern in the memory 130 together with information about a reference time period (e.g., one day, one week, one month, one year, or the like) when the activity pattern is analyzed.

According to various embodiments of the present disclosure, the processor 120 may provide the activity information, the expected value of an activity amount, the probability that an activity goal is achieved, information about a recommended activity, or the like as a feedback. According to an embodiment, the processor 120 may output the pieces of information on the display 160. For example, the processor 120 may combine the pieces of information into a display object (e.g., a text, an image, an icon, a graph, a symbol, a video, or the like) and may output the display object on the display 160. Alternatively, the processor 120 may combine the pieces of information into a voice object and may output the voice object.

The memory 130 may include a volatile memory and/or a nonvolatile memory. The memory 130 may store instructions or data related to at least one of the other elements of the electronic device 101. According to an embodiment of the present disclosure, the memory 130 may store software and/or a program 140. The program 140 may include, for example, a kernel 141, a middleware 143, an application programming interface (API) 145, and/or an application program (or an application) 147. At least a portion of the kernel 141, the middleware 143, or the API 145 may be referred to as an operating system (OS).

The kernel 141 may control or manage system resources (e.g., the bus 110, the processor 120, the memory 130, or the like) used to perform operations or functions of other programs (e.g., the middleware 143, the API 145, or the application program 147). Furthermore, the kernel 141 may provide an interface for allowing the middleware 143, the API 145, or the application program 147 to access individual elements of the electronic device 101 in order to control or manage the system resources.

The middleware 143 may serve as an intermediary so that the API 145 or the application program 147 communicates and exchanges data with the kernel 141.

Furthermore, the middleware 143 may handle one or more task requests received from the application program 147 according to a priority order. For example, the middleware 143 may assign at least one application program 147 a priority for using the system resources (e.g., the bus 110, the processor 120, the memory 130, or the like) of the electronic device 101. For example, the middleware 143 may handle the one or more task requests according to the priority assigned to the at least one application, thereby performing scheduling or load balancing with respect to the one or more task requests.

The API 145, which is an interface for allowing the application 147 to control a function provided by the kernel 141 or the middleware 143, may include, for example, at least one interface or function (e.g., instructions) for file control, window control, image processing, character control, or the like.

An application 147 may include a program described to perform a specific function. For example, the application 147 may include a workout application that measures an exercise amount according to the execution of an exercise and provides the measured exercise amount. Furthermore, the application 147 may be packaged, and the packaged application 147 may be distributed. One or more applications may be installed in the electronic device 101. According to various embodiments of the present disclosure, the application 147 may be installed in the electronic device 101 through various paths. For example, the application 147 may include a preloaded application or a third party application which is downloadable from an external electronic device (e.g., the first external electronic device 102, the second external electronic device 104, or the server 106).

According to various embodiments of the present disclosure, the memory 130 may store the activity information, the activity pattern information, or the like. According to an embodiment, the memory 130 may store the activity information, the activity pattern information, or the like together with time information. According to various embodiments, the memory 130 may store the activity goal. For example, the memory 130 may store the activity goal input from a user through the input/output interface 150. According to various embodiments, the memory 130 may store information about a recommended activity. For example, the memory 130 may store information of a kind of activity, an activity amount per time according to each activity, and the like.

The input/output interface 150 may serve to transfer an instruction or data input from a user or another external device to one or more other elements of the electronic device 101. Furthermore, the input/output interface 150 may output instructions or data received from one or more other elements of the electronic device 101 to the user or another external device.

According to various embodiments of the present disclosure, the input/output interface 150 may include an input device, for example, a touch panel, a physical key, an optical key, a keypad, or the like. According to an embodiment, the input/output interface 150 may receive the activity goal from a user through the input device. According to various embodiments, the input/output interface 150 may include an audio input/output device such as a speaker, a receiver, an earphone, a microphone, or the like. According to an embodiment, the input/output interface 150 may output a voice object corresponding to the activity information, the expected value of an activity amount, the probability that an activity goal is achieved, information about a recommended activity, or the like through an audio output device.

The display 160 may include, for example, a liquid crystal display (LCD), a light-emitting diode (LED) display, an organic LED (OLED) display or plastic OLED (POLED) display, a microelectromechanical systems (MEMS) display, or an electronic paper display. The display 160 may present various content (e.g., a text, an image, a video, an icon, a symbol, or the like) to the user. The display 160 may include a touch screen, and may receive a touch, gesture, proximity or hovering input from an electronic pen or a part of a body of the user. According to various embodiments of the present disclosure, the display 160 may output the activity information, the expected value of an activity amount, the probability that an activity goal is achieved, the information about a recommended activity, or the like.

The communication interface 170 may set communications between the electronic device 101 and an external device (e.g., a first external electronic device 102, a second external electronic device 104, or a server 106). For example, the communication interface 170 may be connected to a network 162 via wireless communications or wired communications so as to communicate with the external device (e.g., the second external electronic device 104 or the server 106).

The wireless communications may employ at least one of cellular communication protocols such as long-term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM). The wireless communications may include, for example, a short-range communication 164. The short-range communications may include at least one of wireless fidelity (Wi-Fi), Bluetooth, near field communication (NFC), magnetic stripe transmission (MST), or GNSS.

The MST may generate pulses according to transmission data and the pulses may generate electromagnetic signals. The electronic device 101 may transmit the electromagnetic signals to a reader device such as a point of sales (POS) device. The POS device may detect the magnetic signals by using a MST reader and restore data by converting the detected electromagnetic signals into electrical signals.

The GNSS may include, for example, at least one of global positioning system (GPS), global navigation satellite system (GLONASS), BeiDou navigation satellite system (BeiDou), or Galileo, the European global satellite-based navigation system according to a use area or a bandwidth. Hereinafter, the term "GPS" and the term "GNSS" may be interchangeably used. The wired communications may include at least one of universal serial bus (USB), high definition multimedia interface (HDMI), recommended standard 232 (RS-232), plain old telephone service (POTS), or the like. The network 162 may include at least one of telecommunications networks, for example, a computer network (e.g., local area network (LAN) or wide area network (WAN)), the Internet, or a telephone network.

The types of the first external electronic device 102 and the second external electronic device 104 may be the same as or different from the type of the electronic device 101. According to an embodiment of the present disclosure, the server 106 may include a group of one or more servers. A portion or all of operations performed in the electronic device 101 may be performed in one or more other electronic devices (e.g., the first electronic device 102, the second external electronic device 104, or the server 106). When the electronic device 101 should perform a certain function or service automatically or in response to a request, the electronic device 101 may request at least a portion of functions related to the function or service from another device (e.g., the first electronic device 102, the second external electronic device 104, or the server 106) instead of or in addition to performing the function or service for itself. The other electronic device (e.g., the first electronic device 102, the second external electronic device 104, or the server 106) may perform the requested function or additional function, and may transfer a result of the performance to the electronic device 101. The electronic device 101 may use a received result itself or additionally process the received result to provide the requested function or service. To this end, for example, a cloud computing technology, a distributed computing technology, or a client-server computing technology may be used.

Figure 1B:
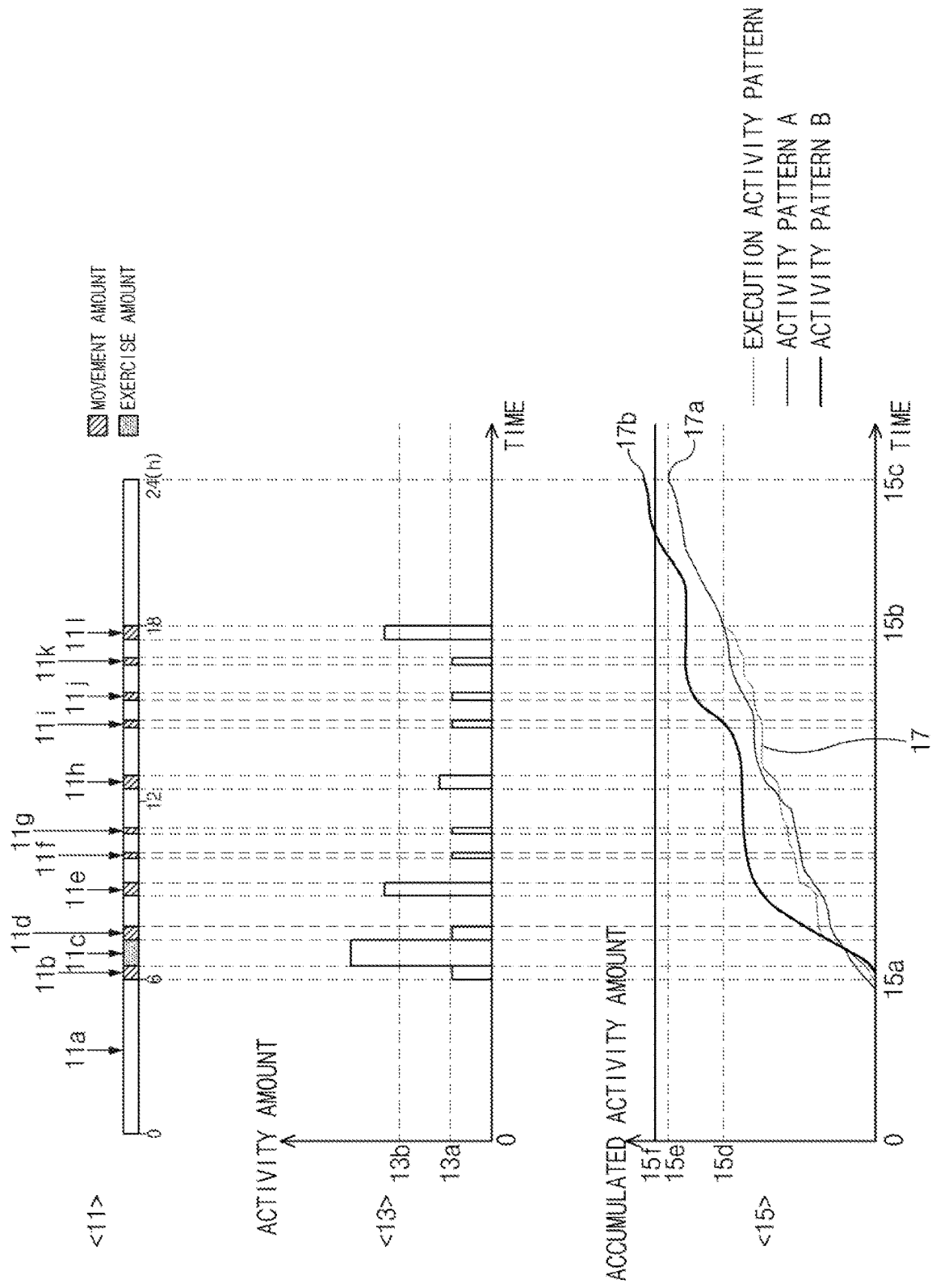
FIG. 1B illustrates a drawing for describing activity information collected during a specific time period according to various embodiments of the present disclosure.

FIG. 1B illustrates a drawing for describing activity information collected during a specific time period according to various embodiments of the present disclosure.

Referring to FIGS. 1A and 1B, the electronic device 101 may analyze an activity pattern based on information about an activity that is performed during a specific time period (e.g., one day). As illustrated in the first graph <11> of FIG. 1B, the electronic device 101 may analyze sensing information collected during the specific time period through the sensor 180 to distinguish an activity amount (e.g., a movement amount or an exercise amount). For example, the electronic device 101 may assign a first activity amount 11b, a third activity amount 11d, a fourth activity amount 11e, a fifth activity amount 11f, a sixth activity amount 11g, a seventh activity amount 11h, an eighth activity amount 11i, a ninth activity amount 11j, a tenth activity amount 11k, an eleventh activity amount 11l, or the like as a movement amount and may assign a second activity amount 11c or the like as an exercise amount. In this regard, the electronic device 101 may distinguish the activity amount based on the characteristic of the sensing information, whether to execute a workout application, or the like. According to various embodiments of the present disclosure, the electronic device 101 may distinguish the activity amount based on time information (e.g., schedule information). According to an embodiment, the electronic device 101 may distinguish an amount of activity (e.g., a sleep activity, an activity of food intake, or the like) (hereinafter referred to as "inactivity"), which is not associated with the measurement of the activity amount, based on the time information. For example, the electronic device 101 may process sensing information, which is collected during a sleep time (e.g., 0 to 6 P.M.) based on the schedule information, as an inactivity amount 11a (which is indicated as various blank portions on the first graph <1>).

According to various embodiments of the present disclosure, the electronic device 101 may distinguish the movement amount or the exercise amount based on a kind of activity. According to an embodiment, the electronic device 101 may distinguish a kind of activity corresponding to the activity amount based on the magnitude of an activity amount. For example, as illustrated in the second graph <13> of FIG. 1B, the electronic device 101 (shown in FIG. 1A) may distinguish the activity amount as an activity amount of walking in the case where the magnitude of the activity amount is smaller than a first magnitude 13a, may distinguish the activity amount as an activity amount of running in the case where the magnitude of the activity amount is greater than or equal to a second magnitude 13b, and may distinguish the activity amount as an activity amount of riding a bicycle or the like in the case where the magnitude of the activity amount is greater than or equal to the first magnitude 13a and is smaller than second magnitude 13b. As illustrated in the second graph 13, the electronic device 101 may distinguish the first activity amount 11b, the third activity amount 11d, the fifth activity amount 11f, the sixth activity amount 11g, the eighth activity amount 11i, the ninth activity amount 11j, the tenth activity amount 11k, or the like as an activity amount of walking and may distinguish the second activity amount 11c, the fourth activity amount 11e, the eleventh activity amount 11l, or the like as an activity amount of running, and may distinguish the seventh activity amount 11h or the like as an activity amount of riding a bicycle.

According to various embodiments of the present disclosure, the electronic device 101 may calculate an accumulated activity amount during a specific time period. As illustrated in the third graph <15>, the electronic device 101 may calculate an accumulated activity amount 15d of activities performed during a specific time period. According to an embodiment, the electronic device 101 may calculate the accumulated activity amount 15d from an activity start time 15a (e.g., 6:00) to a pattern selection time 15b (e.g., 18:00). The pattern selection time 15b may be, for example, a time point when one of activity patterns stored in the memory 130 (shown in FIG. 1A) is selected such that the electronic device 101 calculates the expected value of an activity amount. According to various embodiments, after the activity start time 15a, in the case where a specific time elapses or where the accumulated activity amount 15d is greater than or equal to a specific magnitude, the electronic device 101 may select the specific activity pattern.

According to various embodiments of the present disclosure, the electronic device 101 may analyze an activity pattern (execution activity pattern) 17 during the specific time period (e.g., from the activity start time 15a to the pattern selection time 15b). Furthermore, the electronic device 101 may calculate the expected value of an activity amount by using an activity pattern the same as or similar to the execution activity pattern 17. For example, the electronic device 101 may select an activity pattern the same as or similar to the execution activity pattern 17 of activity patterns (a first activity pattern (or activity pattern a) 17a, a second activity pattern (or activity pattern b) 17b), and the like) stored in the memory 130. As illustrated in the third graph <15>, the electronic device 101 may select the first activity pattern 17a similar to the execution activity pattern 17. In addition, the electronic device 101 may calculate an activity amount, which is from a pattern selection time 15b to a target time 15c, from the selected first activity pattern 17a. The electronic device 101 may calculate the expected value of an activity amount by adding an activity amount '15e-15d', which is calculated from the pattern selection time 15b to the target time 15c, to the accumulated activity amount 15d of the execution activity pattern 17. According to an embodiment, the electronic device 101 may calculate the activity amount '15e-15d', which is obtained by subtracting the accumulated activity amount 15d obtained until the pattern selection time 15b, from the accumulated activity amount 15e obtained until the target time 15c as the expected value of an activity amount.

According to various embodiments of the present disclosure, the electronic device 101 may calculate a probability that an activity goal is achieved, based on a specified activity goal and the expected value of an activity amount. According to an embodiment, the electronic device 101 may calculate a ratio value of an activity goal amount 15f, which corresponds to the activity goal, to the expected value of an activity amount and may assign the ratio value as the probability that an activity goal is achieved, based on the calculated result.

According to various embodiments of the present disclosure, the electronic device 101 may provide a recommended activity corresponding to a recommended activity amount '15f-15d' by which a user works out to achieve the activity goal amount 15f. Alternatively, the electronic device 101 may provide a recommended activity corresponding to an activity amount (an additional amount) obtained by subtracting the expected value of an activity amount from the activity goal amount 15f.

According to various embodiments of the present disclosure, the electronic device 101 may obtain a variety of activity information associated with a user in addition to the activity amount and may provide the user with the obtained activity information. According to an embodiment, the electronic device 101 may determine an activity place by using location information, which is obtained based on a global navigation satellite system (GNSS) while a user is active, and may include the activity place in the activity information. According to an embodiment, the electronic device 101 may determine whether a user is in a room or out a room, by using illuminance information, which is obtained based on an illuminance sensor while a user is active, and may include the determined result in the activity information. According to an embodiment, the electronic device 101 may determine an activity schedule of a user by using schedule information stored in the memory 130 and may include the activity schedule in the activity information.

Figure 2:
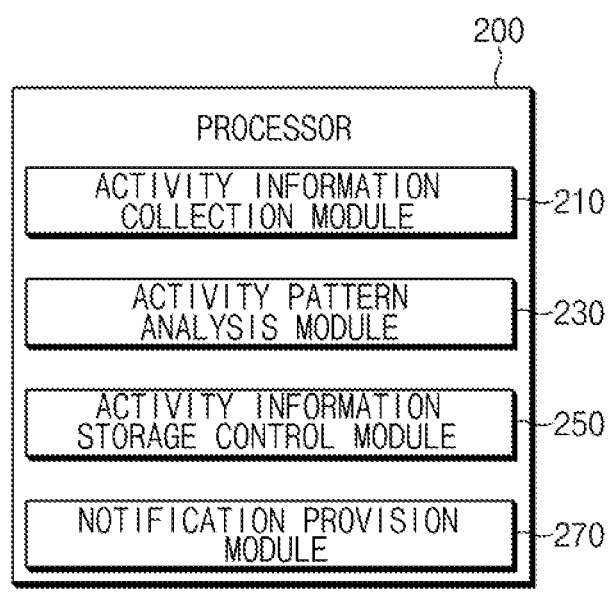
FIG. 2 illustrates a processor associated with providing activity information according to various embodiments of the present disclosure.

FIG. 2 illustrates a processor associated with providing activity information according to various embodiments of the present disclosure. According to various embodiments, the processor 200 may perform a function the same as or similar to that of the processor 120 illustrated in FIG. 1A.

Referring to FIG. 2, the processor 200 may include an activity information collection module 210, an activity pattern analysis module 230, an activity information storage control module 250, and a notification provision module 270. The configuration of the processor 200 illustrated in FIG. 2 is not limited thereto. According to various embodiments of the present disclosure, the processor 200 may include at least another element in addition to the elements. According to an embodiment, at least one of the elements may be omitted.

The activity information collection module 210 may collect activity information including a movement amount and an exercise amount based on a sensor included in an electronic device (e.g., the electronic device 101 shown in FIG. 1A). According to an embodiment, the activity information collection module 210 may collect, for example, a measured value (e.g., an execution time, the intensity of execution, or the like) according to the execution of walking, running, riding a bicycle, or the like. In addition, the activity information collection module 210 may calculate additional information about an activity such as calorie consumption or the like by using the measured value.

According to various embodiments of the present disclosure, the activity information collection module 210 may distinguish the activity information as the movement amount and the exercise amount. According to an embodiment, the activity information collection module 210 may distinguish sensing information, which is collected through the sensor, as the movement amount or the exercise amount based on the characteristic of the sensing information, whether to execute a workout application, time information (e.g., schedule information), or the like.

According to various embodiments of the present disclosure, the activity information collection module 210 may distinguish the activity amount based on a time when the sensing information is collected. According to an embodiment, the activity information collection module 210 may assign sensing information, which is measured while a user works out, as the exercise amount. According to another embodiment, the activity information collection module 210 may not assign sensing information, which is measured while a user sleeps, as the movement amount and the exercise amount. In this regard, the activity information collection module 210 may determine the workout time, the sleep time, and the like of a user by using an activity pattern, time information (e.g., schedule information), and the like. For example, the activity information collection module 210 may determine a time, when an exercise amount is collected during more than a specific time period, as a workout time by verifying a statistical model on an activity. Alternatively, while an exercise amount and a movement amount is not collected during more than a specific time period, the activity information collection module 210 may determine a time period, which is not included in a specific time range (e.g., a daily life time (or a routine time)) based on schedule information, as a sleep time.

According to various embodiments of the present disclosure, with reference to FIG. 2, the activity information collection module 210 may collect information of a kind of activity, an activity amount per time according to each activity, and the like from an external electronic device (e.g., the first external electronic device 102, the second external electronic device 104, or the server 106 shown in FIG. 1A). According to an embodiment, the activity information collection module 210 may collect information of a kind of activity, an activity amount per time according to each activity, and the like from a workout management server (e.g., a server in a fitness club or the like).

According to various embodiments of the present disclosure, the activity information collection module 210 may obtain a variety of activity information associated with a user in addition to the activity amount. According to an embodiment, the activity information collection module 210 may obtain location information based on a GNSS, while a user is active and may determine an activity place based on the location information. Moreover, the activity information collection module 210 may obtain illuminance information based on an illuminance sensor while a user is active and may determine whether a user is in a room or out a room by using the illuminance information. According to an embodiment, the activity information collection module 210 may determine an activity schedule based on schedule information stored in a memory (e.g., the memory 130 shown in FIG. 1A). The activity information collection module 210 may include an activity place, whether a user is in a room or out a room, the activity schedule, or the like in the activity information.

The activity pattern analysis module 230 may analyze an activity pattern based on the collected activity information.

According to an embodiment, the activity pattern analysis module 230 may generate a statistical model on an activity by using pieces of activity information collected during a specific time period (e.g., one day, one week, one month, one year, or the like). For example, the activity pattern analysis module 230 may analyze pieces of activity information, which are stored in a memory (e.g., the memory 130 shown in FIG. 1A), during a specific time period through a cluster analysis, or the like. The activity pattern analysis module 230 may classify pieces of activity amount information corresponding to a reference time period (e.g., one day) into a plurality of groups based on similarity thereof and may calculate a weighted average of the distribution of an activity amount for each group. According to various embodiments of the present disclosure, the activity pattern analysis module 230 may generate the statistical model on an activity during the reference time period by using the calculated weighted average. In addition, when the activity pattern analysis module 230 analyzes the pattern of activity information corresponding to a time period the same as or similar to the reference time period, it may calculate the expected value of an activity amount by comparing the pattern of activity information with a similar pattern of patterns in the statistical model.

According to various embodiments of the present disclosure, the activity pattern analysis module 230 may calculate the expected value of an activity amount, or the like based on the activity information, the activity pattern (e.g., a statistical model on an activity), or the like. According to an embodiment, the activity pattern analysis module 230 may calculate the expected value of an activity amount to be executed until the specified time period ends, by comparing a portion of activity information with the activity pattern during a specified time period (e.g., a target time period). For example, if the specified time period is set to today, the activity pattern analysis module 230 may compare activity information obtained until a specific time (e.g., a current time) of the day, with an activity pattern, of which the reference time period is one day, from among activity patterns. In this case, the activity pattern analysis module 230 may select an activity pattern having time information, which is similar to the specified time period, from among a plurality of activity patterns a reference time period each of which is one day. For example, the activity pattern analysis module 230 may select an activity pattern in which at least one of a year, a month, a day, or a day of the week is the same as the specified time period. In addition, the activity pattern analysis module 230 may extract an activity amount, which corresponds to an activity after the specific time (e.g., a current time), from the selected activity pattern. Moreover, the activity pattern analysis module 230 may assign an activity amount, which is performed after the specific time, that is, the expected value of an activity amount as the extracted activity amount.

According to various embodiments of the present disclosure, the activity pattern analysis module 230 may determine the probability that an activity goal is achieved, by using the expected value of an activity amount and the specified activity goal. According to an embodiment, the activity pattern analysis module 230 may compare the activity goal input from a user with the expected value of an activity amount and may determine the probability that an activity goal is achieved based on the compared result. For example, the activity pattern analysis module 230 may calculate a ratio value of an activity goal amount to a value obtained by summing an activity amount, which is performed until a current time, and the expected value of an activity amount.

According to various embodiments, the activity pattern analysis module 230 may assign the calculated ratio value as the probability that an activity goal is achieved.

According to various embodiments of the present disclosure, the activity pattern analysis module 230 may determine a recommended activity based on the expected value of an activity amount and the probability that an activity goal is achieved. According to an embodiment, the activity pattern analysis module 230 may calculate an activity amount, by which a user works out to achieve the activity goal, and may determine the recommended activity that a user will perform to achieve the activity amount until a target time, based on the calculated result. According to various embodiments, the activity pattern analysis module 230 may determine the recommended activity based on information of a kind of activity, an activity amount per time according to each activity, and the like. According to various embodiments, the activity pattern analysis module 230 may use the information of a kind of activity, an activity amount per time according to each activity, and the like collected from an external electronic device (e.g., the first external electronic device 102, the second external electronic device 104, or the server 106, shown in FIG. 1A) or may use the information previously stored in a memory (e.g., the memory 130 shown in FIG. 1A), through the activity information collection module 210.

According to various embodiments of the present disclosure, the activity pattern analysis module 230 may determine the recommended activity by using an activity place, whether a user is in a room or out a room, an activity schedule, or the like included in the activity information. According to an embodiment, the activity pattern analysis module 230 may determine a kind of proper workout, which is performed at the activity place, and may determine the recommended activity based on the determined result. According to an embodiment, the activity pattern analysis module 230 may determine whether a user is in a room or out a room and may determine the recommended activity based on the determined result. According to an embodiment, the activity pattern analysis module 230 may determine the recommended activity by verifying the activity schedule of a user. For example, the activity pattern analysis module 230 may calculate a time, which remains until the target time, based on the activity schedule, and in the case where the remaining time is smaller than a specific time, it may determine an activity, of which the activity amount per time is high, as a recommended activity.

The activity information storage control module 250 may store the collected activity information, the analyzed activity pattern, or the like in a memory (e.g., the memory 130 shown in FIG. 1A). According to an embodiment, the activity information storage control module 250 may control the memory such that the activity information, the activity pattern, or the like is stored together with time information. For example, the activity information storage control module 250 may sequentially store the activity information in the memory together with the collected time information. Furthermore, the activity information storage control module 250 may store the activity pattern in the memory together with a reference time period (e.g., one day, one week, one month, one year, or the like) when the activity pattern is analyzed. In addition, the activity information storage control module 250 may store an activity goal, which is input from a user, in the memory. According to various embodiments of the present disclosure, the activity information storage control module 250 may store information, which is collected through the activity information collection module 210, of a kind of activity, an activity amount per time according to each activity, and the like in the memory.

The notification provision module 270 may provide a notification on the activity information, the expected value of an activity amount, the probability that an activity goal is achieved, information about a recommended activity, or the like. According to an embodiment, the notification provision module 270 may output the pieces of information on a display (e.g., the display 160 shown in FIG. 1A). For example, the notification provision module 270 may combine the pieces of information into a display object and may output the display object on the display. According to various embodiments of the present disclosure, the notification provision module 270 may combine the pieces of information into a voice object and may output the voice object through an audio output device.

According to various embodiments of the present disclosure, the notification provision module 270 may provide the activity information for each interval or in response to a user input (e.g., a selection input of an icon set to provide activity information, or the like), or the like. According to an embodiment, in the case where the change in the activity amount is out of the specific range, the notification provision module 270 may provide the activity information. Furthermore, when the activity information is provided, the notification provision module 270 may provide the expected value of an activity amount, the probability that an activity goal is achieved, information about a recommended activity, or the like together. According to various embodiments, the probability that an activity goal is achieved is less than or equal to a specific value, the notification provision module 270 may combine the pieces of information into a voice object and may output the voice object through an audio output device together as well as combining the pieces of information into a display object and outputting the display object on the display. Furthermore, in the case where the probability that an activity goal is achieved is less than the specific value, the notification provision module 270 may provide information about a recommended activity.

According to various embodiments of the present disclosure, the notification provision module 270 may provide a notification on the activity information, the expected value of an activity amount, the probability that an activity goal is achieved, information about a recommended activity, or the like to an external electronic device (e.g., the first external electronic device 102, the second external electronic device 104, or the server 106, shown in FIG. 1A).

As described above, according to various embodiments of the present disclosure, an electronic device may include a sensor configured to collect sensing information according to a motion of the electronic device, and a processor operatively connected with the sensor. The processor may be configured to obtain activity information including at least one of an exercise amount that is calculated based on first sensing information obtained according to execution of a specified workout, and a movement amount that is calculated based on second sensing information obtained according to a daily life, determine an expected value of an activity amount, by which a user works out, during a specific time period by a user based on the activity information, and provide guide information for achieving an activity goal associated with the user based on at least one of the expected value of the activity amount and the activity information.

According to various embodiments of the present disclosure, the processor may be configured to analyze an activity pattern of the user based on the activity information.

According to various embodiments of the present disclosure, the processor may be configured to determine the expected value of the activity amount based on the activity pattern.

According to various embodiments of the present disclosure, the processor may be configured to determine a probability of achievement with respect to the activity goal based on the expected value of the activity amount and to provide a notification on the probability of achievement.

According to various embodiments of the present disclosure, the processor may be configured to provide information about the activity pattern together when the processor provides the notification on the probability of achievement.

According to various embodiments of the present disclosure, the processor may be configured to provide a feedback on the activity information based on the expected value of the activity amount.

According to various embodiments of the present disclosure, the processor may be configured to provide the feedback by using a visual effect corresponding to at least one of the activity goal, the activity information, and the expected value of the activity amount.

According to various embodiments of the present disclosure, the guide information may further include guide information about a second activity different from a first activity associated with the activity goal.

According to various embodiments of the present disclosure, the guide information about the second activity may include at least one of a kind of the second activity, an activity amount per time of the second activity, a recommended activity time of the second activity, recommended activity intensity of the second activity, and an execution schedule of the second activity.

According to various embodiments of the present disclosure, the processor may be configured to provide the guide information to an external electronic device connected through a communication interface.

Figure 3:
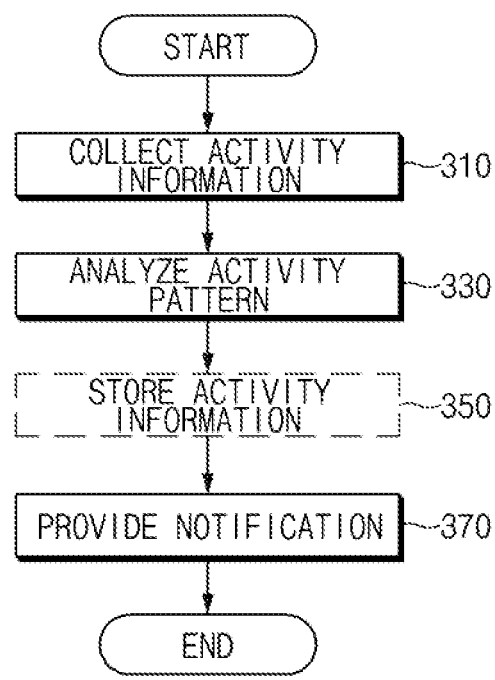
FIG. 3 illustrates a method of operating an electronic device which is associated with providing activity information according to various embodiments of the present disclosure.

FIG. 3 illustrates a method of operating an electronic device, which is associated with providing activity information according to various embodiments of the present disclosure.

Referring to FIG. 3, in operation 310, the electronic device (e.g., the electronic device 101 shown in FIG. 1A or the activity information collection module 210 shown in FIG. 2) may collect the activity information. According to an embodiment, the electronic device may collect the activity information for each interval or in response to a user input or the like.

In operation 330, the electronic device (e.g., the activity pattern analysis module 230 shown in FIG. 2) may analyze an activity pattern. For example, the electronic device may analyze the pattern of the collected activity information. According to an embodiment, the electronic device may analyze the pattern of the pieces of activity information from an activity start time (e.g., 6 A.M.) to a specific time (e.g., a current time) during a specified time period (e.g., one day). The specified time period may include, for example, a time period from the activity start time to a target time input from a user. According to various embodiments of the present disclosure, the electronic device may analyze the patterns of pieces of activity information performed during a specific time period (e.g., one day, one week, one month, one year, or the like) and may generate a statistical model on the activity during the specific time period based on the analyzed result.

In operation 350, which may be optional, the electronic device (e.g., the activity information storage control module 250) may store the activity information in a memory (e.g., the memory 130 in FIG. 1A). According to an embodiment of the present disclosure, the electronic device may store the activity information in the memory together with the collected time information. According to various embodiments, the electronic device may store the activity pattern (e.g., the statistical model on an activity during the specific time period). According to an embodiment, the electronic device may store the activity pattern in the memory together with the specific time period information. According to an embodiment, operation 350 may be omitted.

In operation 370, the electronic device (e.g., the notification provision module 270 (shown in FIG. 2) may provide a notification on the activity information. According to an embodiment, the electronic device may provide pieces of activity information collected from an activity start time to a specific time during a specified time period. For example, the electronic device may combine a kind, an execution time, the intensity of execution, calorie consumption, or the like of an activity, which is performed from an activity start time to a specific time, into a display object and may output the display object on a display (e.g., the display 160 shown in FIG. 1A) or may combine it into a voice object and may output the voice object through an audio output device.

According to various embodiments of the present disclosure, in operation 330, the electronic device (e.g., the activity pattern analysis module 230 shown in FIG. 2) may determine the expected value of an activity amount, a probability that an activity goal is achieved, a recommended activity, or the like. In addition, in operation 370, when the electronic device provides a notification on the activity information, it may provide the expected value of an activity amount, a probability that an activity goal is achieved, information about a recommended activity, or the like.

According to various embodiments of the present disclosure, the electronic device may provide the activity information, the expected value of an activity amount, the probability that an activity goal is achieved, the information about a recommended activity, or the like to an external electronic device (e.g., the first external electronic device 102, the second external electronic device 104, or the server 106, shown in FIG. 1A).

Figure 4:
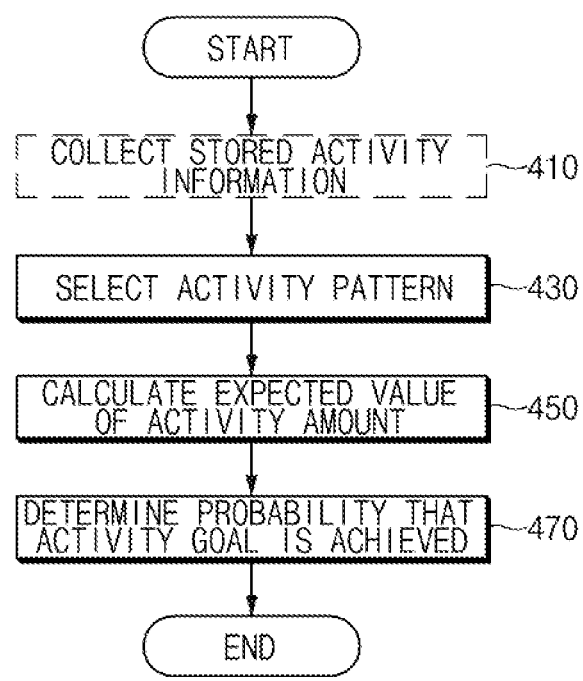
FIG. 4 illustrates an example of a method of operating an electronic device which is associated with providing activity information about an activity goal according to various embodiments of the present disclosure.

FIG. 4 illustrates an example of a method of operating an electronic device, which is associated with providing activity information about an activity goal, according to various embodiments of the present disclosure. According to various embodiments, when the electronic device (e.g., the electronic device 101 shown in FIG. 1A) provides a notification of collected activity information, it may provide the expected value of an activity amount, probability that an activity goal is achieved, information about a recommended activity, or the like together. For example, when the electronic device performs operations associated with providing the activity information illustrated in FIG. 3, it may provide the pieces of information together.

Referring to FIG. 4, in operation 410, which may be optional, the electronic device (e.g., the electronic device 101 in FIG. 1A or the activity information collection module 210) may collect activity information stored in a memory (e.g., the memory 130 in FIG. 1A). For example, the electronic device may collect the pieces of activity information, which is stored in the memory, during a specific time period. According to an embodiment, the electronic device may analyze the patterns of the pieces of collected activity information and may generate a statistical model on an activity during the specific time period by using the analyzed patterns. According to various embodiments of the present disclosure, the electronic device may collect an activity pattern (e.g., the statistical model on the activity during the specific time period) stored in the memory. According to an embodiment, operation 410 may be omitted.

According to various embodiments of the present disclosure, the electronic device may perform operations 410, 430, 450, and 470 in connection with performance of operations associated with providing activity information illustrated in FIG. 3. According to an embodiment, the electronic device may perform operations 410, 430, 450, and 470 in synchronization with performance of operation 330 (shown in FIG. 3) or after a specific interval. According to an embodiment, in the case where the operations in FIG. 4 are connected with performance of operations associated with providing the activity information illustrated in FIG. 3, the electronic device may omit operation 410. In this case, the electronic device may use the activity information collected in operation 310.

In operation 430, the electronic device (e.g., the activity pattern analysis module 230 shown in FIG. 2) may select an activity pattern. According to an embodiment, the electronic device may select an activity pattern, which has information about a time similar to the specific time period, from among the collected or analyzed activity patterns. For example, the electronic device may select an activity pattern in which at least one of a year, a month, a day, or a day of the week is the same as the specific time period.

In operation 450, the electronic device (e.g., the activity pattern analysis module 230 shown in FIG. 2) may calculate the expected value of an activity amount. The expected value of an activity amount may include an activity amount, by which a user works out, during a specified time period (e.g., a time period from an activity start time to a target time) included in an activity goal input from a user. Alternatively, the expected value of an activity amount may include an activity amount, by which a user works out, from a specific time (e.g., a current time) to the target time. According to various embodiments of the present disclosure, the electronic device may calculate the expected value of an activity amount based on the selected activity pattern. For example, the electronic device may extract an activity amount, which was performed during the specified time period, from the selected activity pattern and may assign the extracted activity amount as the expected value of an activity amount. Alternatively, the electronic device may extract an activity amount, which corresponds to an activity after the specific time, from the selected activity pattern and may assign the extracted activity amount as the expected value of an activity amount.

In operation 470, the electronic device (e.g., the activity pattern analysis module 230 shown in FIG. 2) may determine a probability that an activity goal is achieved. The probability that an activity goal is achieved may include information in which a probability that the specified activity goal is achieved during a specified time period is expressed as a value (e.g., a percentage). According to various embodiments of the present disclosure, the electronic device may determine the probability that an activity goal is achieved, based on the expected value of an activity amount and the specified activity goal. According to an embodiment, the electronic device may calculate a ratio value of an activity goal amount to a value obtained by summing an activity amount, which is performed until a current time, and the expected value of an activity amount and may assign the calculated ratio value as the probability that an activity goal is achieved.

Figure 5:
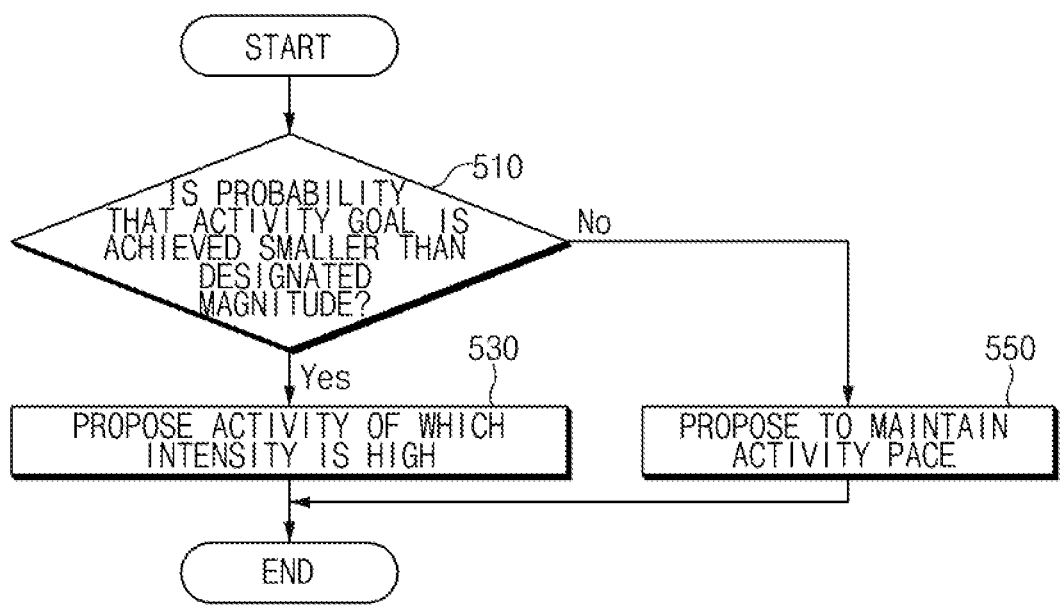
FIG. 5 illustrates an example of a method of operating an electronic device which is associated with an activity guide according to various embodiments of the present disclosure.

FIG. 5 illustrates an example of a method of operating an electronic device which is associated with an activity guide according to various embodiments of the present disclosure. According to various embodiments, the electronic device (e.g., the electronic device 101 shown in FIG. 1A) may determine a recommended activity based on the expected value of an activity amount and a probability that an activity goal is achieved and may provide an activity guide on the recommended activity based on the determine recommendation activity.

Referring to FIG. 5, in operation 510, the electronic device may determine whether the probability that an activity goal is achieved is smaller than a specific magnitude (e.g., 70%). According to various embodiments of the present disclosure, in the case where the probability that an activity goal is achieved is smaller than the specific magnitude, in operation 530, the electronic device (e.g., the notification provision module 270 shown in FIG. 2) may propose an activity, of which the intensity is higher than that of an activity that is currently performed, as a recommended activity. According to an embodiment, in the case where the expected value of an activity amount does not reach an activity goal that a user set, the electronic device may propose an activity, of which the intensity is higher than that of an activity corresponding to the expected value of an activity amount, as a recommended activity. According to various embodiments of the present disclosure, the electronic device may determine the recommended activity by using information, which is stored in a memory (e.g., the memory 130 shown in FIG. 1A), of a kind of activity, an activity amount per time according to each activity, and the like. For example, the electronic device may verify a time, which remains until a target time, and may determine whether a value, which is obtained by multiplying the remaining time by an activity amount per time according to each activity, satisfies a specified activity goal. As such, the electronic device may assign an activity, in which the obtained value satisfies the specified activity goal, as a recommended activity.

According to various embodiments of the present disclosure, in the case where the probability that an activity goal is achieved is greater than or equal to the specific magnitude, in operation 550, the electronic device (e.g., the notification provision module 270 shown in FIG. 2) may propose to maintain a current activity pace. According to an embodiment, in the case where the probability that an activity goal is achieved is greater than a specific magnitude (e.g., 90%), the electronic device may propose an activity, of which the intensity is lower than that of an activity that is currently performed, as a recommended activity. Alternatively, the electronic device may propose to take a break during a specific time.

As described above, according to various embodiments of the present disclosure, a method may include collecting sensing information according to a motion of an electronic device, obtaining activity information comprising at least one of an exercise amount that is calculated based on first sensing information obtained according to execution of a specified workout, and a movement amount that is calculated based on second sensing information obtained according to a daily life, determining an expected value of an activity amount, by which a user works out, during a specific time period by a user, based on the activity information, and providing guide information for achieving an activity goal associated with the user based on at least one of the expected value of the activity amount and the activity information.

According to various embodiments of the present disclosure, the method may further include analyzing an activity pattern of the user based on the activity information.

According to various embodiments of the present disclosure, the determining of the expected value of the activity amount may include determining the expected value of the activity amount based on the activity pattern.

According to various embodiments of the present disclosure, the method may further include determining a probability of achievement with respect to the activity goal based on the expected value of the activity amount, and providing a notification on the probability of achievement.

According to various embodiments of the present disclosure, the providing of the notification may further include providing information about the activity pattern.

According to various embodiments of the present disclosure, the method may further include providing a visual effect corresponding to at least one of the activity goal, the activity information, and the expected value of an activity amount as a feedback.

According to various embodiments of the present disclosure, the providing of the guide information may further include providing guide information about a second activity different from a first activity associated with the activity goal.

According to various embodiments of the present disclosure, the providing of the guide information about the second activity may include comprising at least one of a kind of the second activity, an activity amount per time of the second activity, a recommended activity time of the second activity, recommended activity intensity of the second activity, and an execution schedule of the second activity and providing the comprised at least one.

According to various embodiments of the present disclosure, the providing of the guide information may further include providing the guide information to an external electronic device connected through a communication interface.

Figure 6:
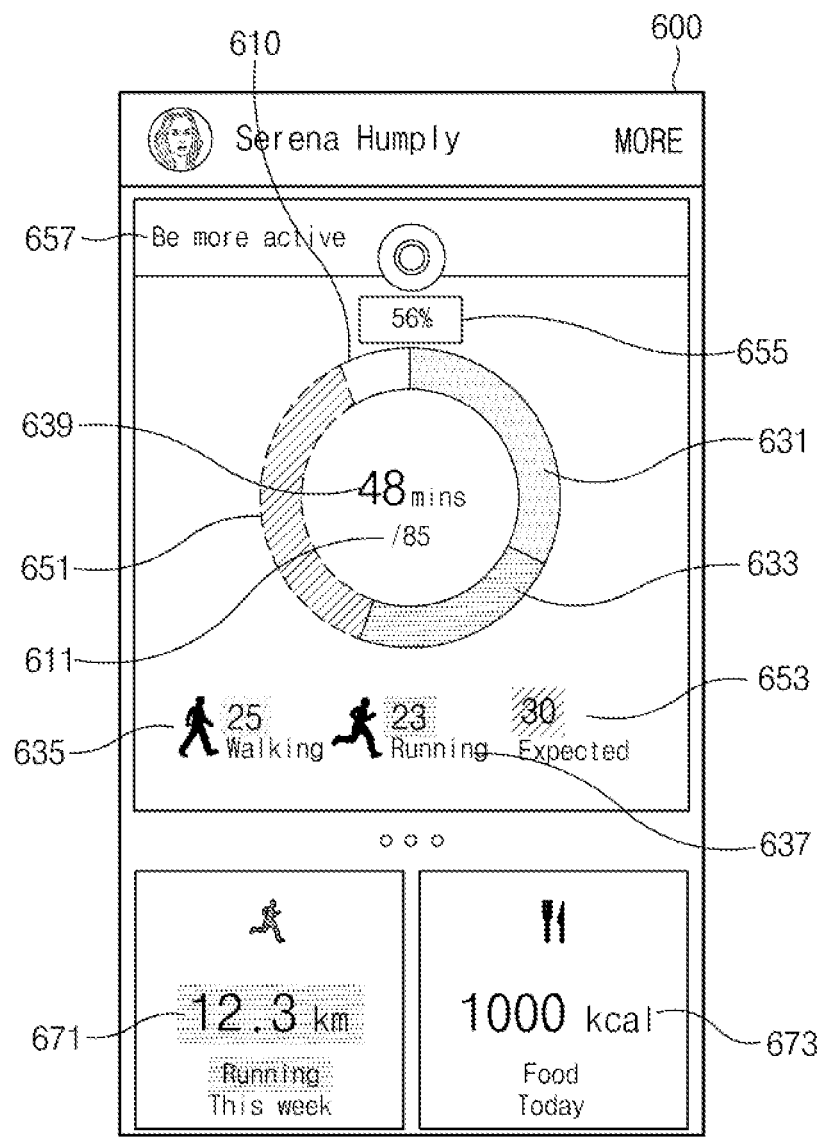
FIG. 6 illustrates an example of a screen for providing activity information about an activity goal according to various embodiments of the present disclosure.

FIG. 6 illustrates an example of a screen for providing activity information about an activity goal according to various embodiments of the present disclosure. According to various embodiments, the electronic device (e.g., the electronic device 101 shown in FIG. 1A) may output an activity information provision screen 600 on a display (e.g., the display 160 shown in FIG. 1A) for each interval or in response to a user input (e.g., an input for selecting an object (e.g., an icon) set to provide activity information) or the like.

Referring to FIG. 6, the activity information provision screen 600 may include an activity goal graph 610 in a specific area (e.g., a center area). The activity goal graph 610 may be an object, which represents an activity goal input from a user expressed as a graph. According to an embodiment, the activity goal graph 610 may be generated in the form of a circle and may express an activity amount through a specific angle in the circle, a length of a circular arc on the circumference, or the like. However, the form of the activity goal graph 610 is not limited thereto. According to various embodiments of the present disclosure, the activity goal graph 610 may be generated in the form of a line, a bar, an oval, or the like. The drawing illustrates a state in which the activity goal graph 610 is output in the form of a doughnut in the circle and is output on a part of an area of the doughnut such that a first activity amount 631 (e.g., activity amount of walking) accumulated until a specific time (e.g., a current time), a second activity amount 633 (e.g., an activity amount of running) accumulated until a specific time, and an expected value of an activity amount 651 correspond to a ratio on an activity goal amount set to the activity goal. According to an embodiment, the first activity amount 631 or the second activity amount 633 may be replaced by a movement amount or an exercise amount. The donut shape of the activity goal graph 610 illustrated in FIG. 6 is for illustrative purposes and not limited thereto. Other shapes or formats, such as a bar graph or text may be substituted, according to the preference of the user.

According to various embodiments of the present disclosure, the activity information provision screen 600 may include an activity goal displaying object 611 displayed on a specific area (e.g., a center area), a first detailed information displaying object 635 corresponding to the first activity amount 631, a second detailed information displaying object 637 corresponding to the second activity amount 633, an accumulated activity amount displaying object 639, a detailed information displaying object 653 of the expected value of an activity amount 651, an object 655 for displaying a probability that an activity goal is achieved, an activity pace adjustment notification object 657, and the like.

The activity goal displaying object 611 may include a text, an image, an icon, or the like corresponding to the activity goal. According to an embodiment, the activity goal displaying object 611 may include a target time, an activity goal amount, or the like included in the activity goal. The drawing illustrates a state in which the activity goal displaying object 611 is generated with a text corresponding to a target time and is output on the center area of the activity goal graph 610. According to various embodiments of the present disclosure, the activity goal displaying object 611 may be displayed on or below the activity goal graph 610.

The first detailed information displaying object 635 and the second detailed information displaying object 637 may include detailed information of the first activity amount 631 and the second activity amount 633 which are accumulated until the specific time. According to an embodiment, the first detailed information displaying object 635 and the second detailed information displaying object 637 may include a text, an image, an icon, or the like corresponding to a kind, an execution time, the intensity of execution, calorie consumption, or the like of an activity of the first activity amount 631 and the second activity amount 633. The drawing illustrates a state in which each of the first detailed information displaying object 635 and the second detailed information displaying object 637 outputs the kind of activity amount and the activity time below the activity goal graph 610. According to various embodiments of the present disclosure, the first detailed information displaying object 635 or the second detailed information displaying object 637 may be output with a color or a background color the same as or similar to a background color of the area of the first activity amount 631 or the second activity amount 633 that are output on the activity goal graph 610 with a specific area. According to various embodiments, the activity information provision screen 600 may output a detailed information displaying object of another activity amount (e.g., a third activity amount) in addition to the first activity amount 631 and the second activity amount 633.

The accumulated activity amount displaying object 639 may include the total sum of activity amounts accumulated until a specific time. According to an embodiment, the accumulated activity amount displaying object 639 may the total sum of an execution time, the intensity of execution, calorie consumption, or the like included in activity information. The drawing illustrates a state in which the accumulated activity amount displaying object 639 is generated with a text corresponding to the total sum of an execution time included in activity information and is output to be adjacent to the activity goal displaying object 611.

The detailed information displaying object 653 of the expected value of an activity amount 651 may include an activity time, an activity amount, or the like corresponding to the expected value of an activity amount 651. The drawing illustrates a state in which the detailed information displaying object 653 of the expected value of an activity amount 651 is generated with a text corresponding to the activity time and is output to be adjacent to the first detailed information displaying object 635 and the second detailed information displaying object 637.

The object 655 for displaying a probability that an activity goal is achieved may include a text, an image, an icon, or the like corresponding to the probability that an activity goal is achieved. The drawing illustrates a state in which the object 655 for displaying a probability that an activity goal is achieved is generated with a text corresponding to the probability that an activity goal is achieved and is output on the activity goal graph 610.

The activity pace adjustment notification object 657 may include a text, an image, an icon, or the like corresponding to whether to adjust an activity pace. According to an embodiment, as illustrated in FIG. 6, in the case where the probability that an activity goal is achieved is less than or equal to a specific value, the activity pace adjustment notification object 657 may output a first text (e.g., "increase an activity pace") on the activity information provision screen 600. Alternatively, in the case where the probability that an activity goal is achieved is greater than the specific value, the activity pace adjustment notification object 657 may include a second text (e.g., "maintain an activity pace"). According to various embodiments of the present disclosure, the activity pace adjustment notification object 657 may differently output a text color, a kind of image, a kind of icon, a background color, or the like based on the probability that an activity goal is achieved. According to an embodiment, the electronic device may change at least one of a background, an effect, or a theme of the activity information provision screen 600 instead of outputting the activity pace adjustment notification object 657.

According to various embodiments of the present disclosure, the activity information provision screen 600 may include a detailed information displaying object 671 of a specific activity performed during a specific time period, a detailed information displaying object 673 of inactivity, or the like on a specific area (e.g., a lower end area). The detailed information displaying object 671 of the specific activity represents, for example, detailed information of a first activity amount or a second activity amount during the specific time period (e.g., one day, one week, one month, one year, or the like). The drawing illustrates a state in which the detailed information displaying object 671 of the specific activity outputs detailed information about a second activity amount (e.g., an activity amount of running) during one week with a text, an image, and the like. The detailed information displaying object 673 of the inactivity may include, for example, detailed information according to a sleep activity or an activity of food intake. The drawing illustrates a state in which the detailed information displaying object 673 of the inactivity outputs the variation in a calorie according to food intake with a text, an image, and the like.

According to various embodiments of the present disclosure, in the case where the number of kinds of specific activities is greater than a specific number, the activity information provision screen 600 may control a display such that the detailed information displaying object 671 of the specific activity or the detailed information displaying object 673 of the inactivity that is output on a lower end area is output with a page format. According to an embodiment, the activity information provision screen 600 may output a detailed information displaying object of the activity on different pages for each kind of activity. Accordingly, if a user input for turning over a page or a user input for selecting a page different from a page is currently output is generated, the electronic device may output a detailed information displaying object of the activity included in the selected page.

According to various embodiments of the present disclosure, the electronic device may omit at least one of elements included in the activity information provision screen 600 or may include at least other elements, based on the probability that an activity goal is achieved. According to an embodiment, in the case where the probability that an activity goal is achieved is smaller than or equal to a specific value, the electronic device may control a display such that the detailed information displaying object 653 of the expected value of an activity amount 651 or the object 655 for displaying a probability that an activity goal is achieved is not output. According to an embodiment, in the case where the probability that an activity goal is achieved is smaller than or equal to a specific value, the electronic device may control the display such that the activity information provision screen 600 is not output. According to various embodiments, the electronic device may output a voice object corresponding to at least one element together with the output of elements included in the activity information provision screen 600.

Figure 7:
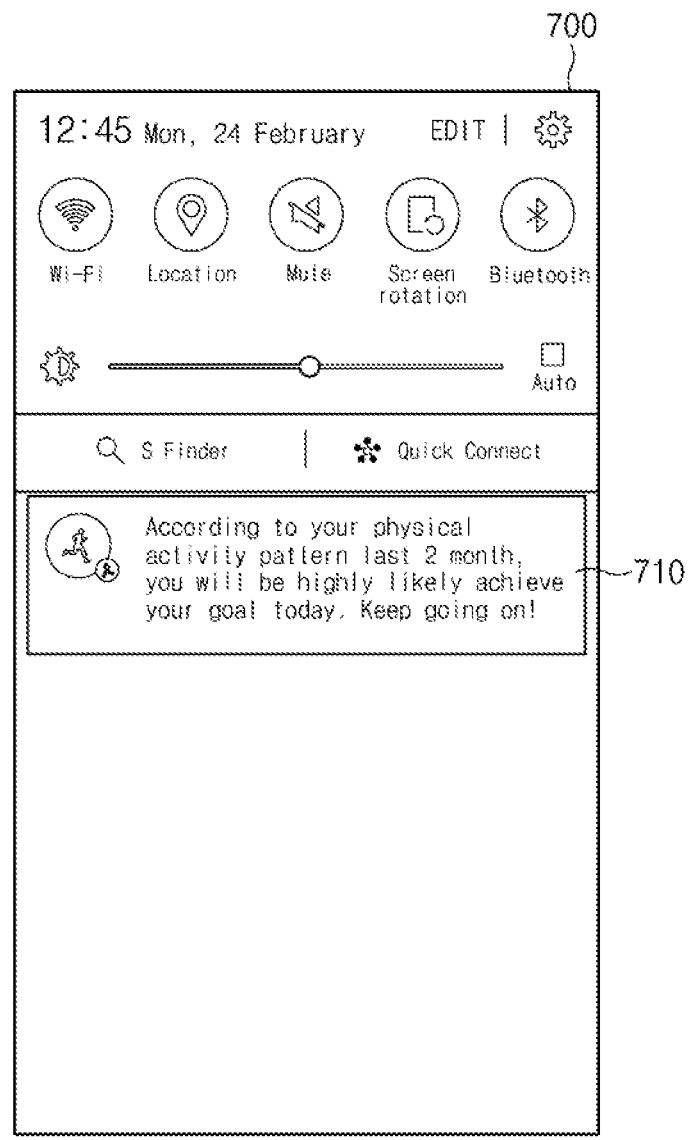
FIG. 7 illustrates an example of a notification screen associated with providing activity information according to various embodiments of the present disclosure.

FIG. 7 illustrates an example of a notification screen associated with providing activity information according to various embodiments of the present disclosure.

Referring to FIG. 7, the electronic device (e.g., the electronic device 101 shown in FIG. 1A) may output a notification screen 700 on a probability that an activity goal is achieved. For example, the electronic device may output the notification object 710 including a text, an image, an icon, or the like corresponding to the probability that an activity goal is achieved, on a specific area (e.g., a center area) of the notification screen 700. According to various embodiments of the present disclosure, while a specific screen (e.g., a home screen) is output, in the case where the probability that an activity goal is achieved satisfies a specific condition (e.g., more than a specific value), the electronic device may switch the specific screen to the notification screen 700. Alternatively, the electronic device may output the notification object 710 on the specific screen in the form of a pop-up. In this case, the electronic device may blurredly output or transparently output the specific screen.

According to various embodiments of the present disclosure, the notification object 710 may further include a cheering message for assisting the goal achievement of a user together with information corresponding to the probability that an activity goal is achieved. According to various embodiments, the electronic device may output a voice object corresponding to at least one of information corresponding to the probability that an activity goal is achieved or the cheering message together with the output of the notification object 710.

Figure 8:
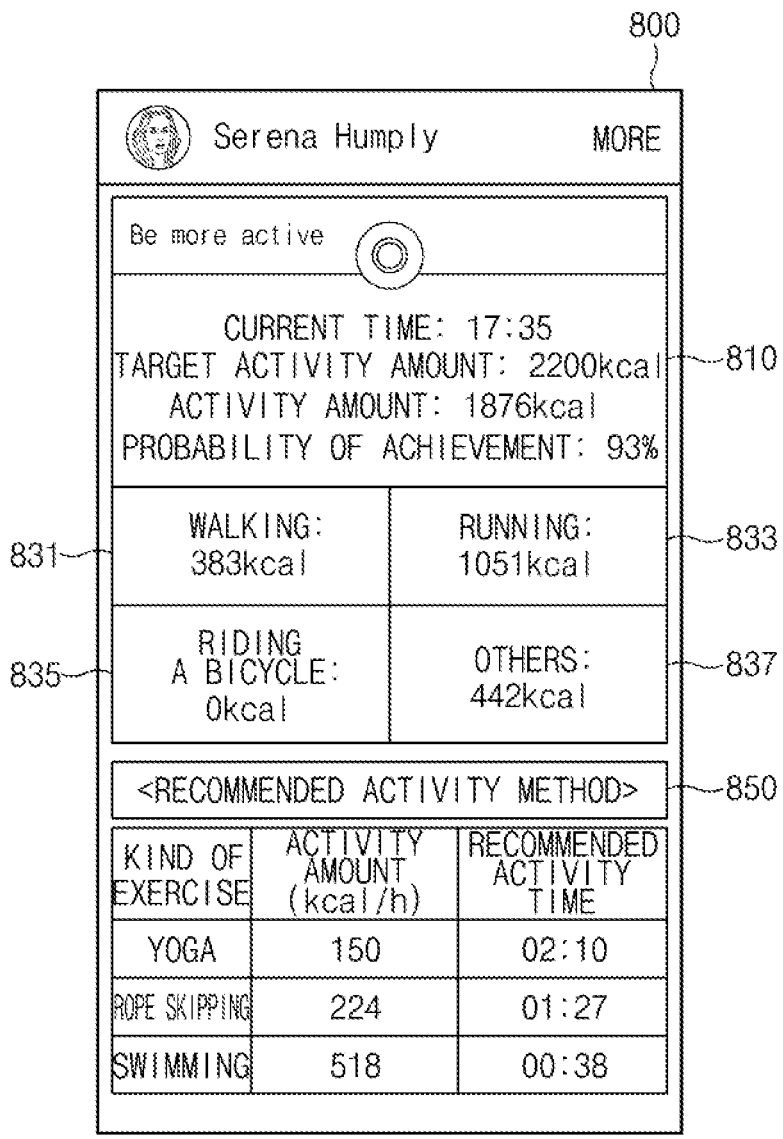
FIG. 8 illustrates an example of an activity information screen associated with providing activity information according to various embodiments of the present disclosure.

FIG. 8 illustrates an example of an activity information screen associated with providing activity information according to various embodiments of the present disclosure.

Referring to FIG. 8, in the case where a probability that an activity goal is achieved satisfies a specific condition (e.g., more than a specific value), the electronic device (e.g., the electronic device 101 shown in FIG. 1A) may output an activity guide screen 800. Alternatively, after the output of the activity information provision screen 600 illustrated in FIG. 6, in the case where a specific user input occurs or where a specific time elapses, the electronic device may switch the activity information provision screen 600 to the activity guide screen 800. According to an embodiment, after the output of the notification screen 700 illustrated in FIG. 7, in the case where a specific user input (e.g., an input for selecting the notification object 710 shown in FIG. 7) occurs or where a specific time elapses, the electronic device may switch the notification screen 700 to the activity guide screen 800.

The activity guide screen 800 may include an activity information displaying object 810, a first activity amount displaying object 831, a second activity amount displaying object 833, a third activity amount displaying object 835, a detailed information displaying object 837 of inactivity, a recommended activity displaying object 850, and the like. The activity information displaying object 810 may include a text, an image, an icon, or the like corresponding to a current time, an activity goal, an accumulated activity amount, the expected value of an activity amount, a probability that an activity goal is achieved, or the like.

Each of the first activity amount displaying object 831, the second activity amount displaying object 833, and the third activity amount displaying object 835 may include a corresponding activity amount. The drawing illustrates a state in which each of the first activity amount displaying object 831, the second activity amount displaying object 833, and the third activity amount displaying object 835 is output with the activity amount changed into calorie consumption. According to various embodiments of the present disclosure, the activity guide screen 800 may include an activity amount displaying object on an activity except a first activity amount (e.g., activity amount of walking), a second activity amount (e.g., an activity amount of running), and a third activity amount (e.g., an activity amount of riding a bicycle). According to an embodiment, the activity guide screen 800 may include displaying objects, and in each of the displaying objects, the first activity amount, the second activity amount, the third activity amount, or the like may be distinguished as a movement amount and an exercise amount.

The detailed information displaying object 837 of inactivity may include detailed information about an activity (e.g., a sleep activity, an activity of food intake, or the like) regardless of the measurement of an activity amount. The drawing illustrates a state in which the detailed information displaying object 837 of inactivity is output with calorie consumption or the like according to the inactivity.

The recommended activity displaying object 850 may include a recommended activity method. According to an embodiment, the recommended activity displaying object 850 may include information of a kind of activity, an activity amount per time according to each activity, a recommended activity time, recommended activity intensity, a schedule, or the like. According to various embodiments of the present disclosure, the recommended activity displaying object 850 may include a list, a table, or the like in which information about each activity is composed of one item. According to an embodiment, the recommended activity displaying object 850 may include only an activity method on a recommended activity, of which the recommended activity time is shortest, from among a plurality of recommended activities.

Figure 9:
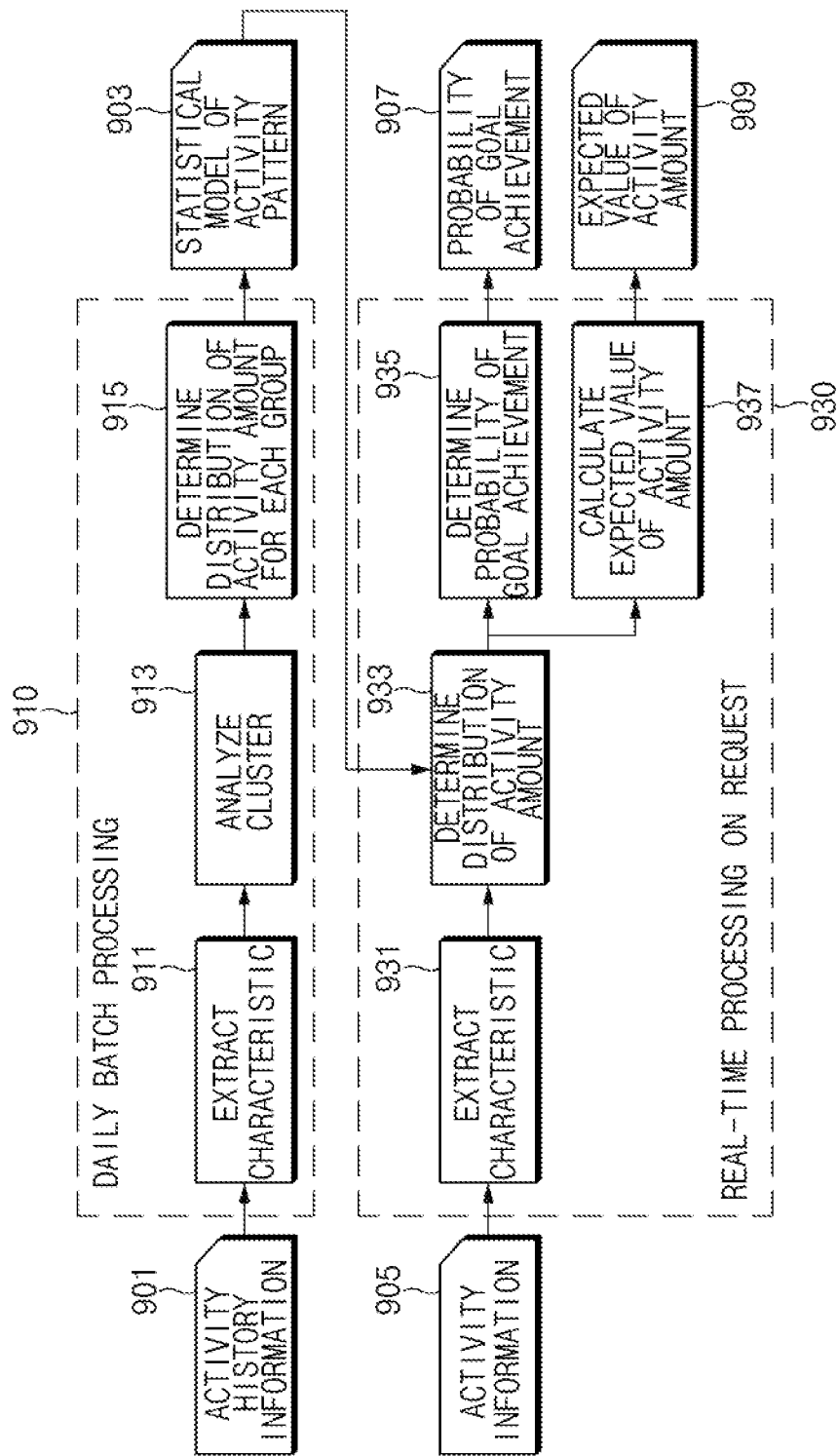
FIG. 9 illustrates a drawing for describing an example of providing activity information by using an activity pattern according to various embodiments of the present disclosure.

FIG. 9 illustrates a drawing for describing an example of providing activity information by using an activity pattern according to various embodiments of the present disclosure.

Referring to FIG. 9, the electronic device (e.g., the electronic device 101 shown in FIG. 1A) may generate a statistical model 903 of an activity pattern based on activity history information 901. Furthermore, the electronic device may determine a probability of goal achievement 907 or an expected value of an activity amount 909 based on activity information 905 and the statistical model 903 of an activity pattern.

According to various embodiments of the present disclosure, the electronic device may generate an activity pattern (e.g., the statistical model 903 of an activity pattern) based on activity information (e.g., the activity history information 901), which is stored in a memory (e.g., the memory 130 shown in FIG. 1A), during a specific time period. For example, the electronic device may perform a batch processing (e.g., a daily batch processing 910) function for each specific time period.

According to the daily batch processing 910, in operation 911, the electronic device (e.g., the activity pattern analysis module 230 shown in FIG. 2) may extract the characteristic of the activity history information 901. According to an embodiment, the electronic device may extract the characteristic vector of the activity history information 901. For example, the electronic device may distinguish the activity history information 901 as an activity amount according to a time and may extract a characteristic vector by connecting amounts of activities of a time when an activity amount rapidly increases (e.g., the variation in an activity amount on a time variation is greater than a specific magnitude).

In operation 913, the electronic device (e.g., the activity pattern analysis module 230 shown in FIG. 2) may perform a cluster analysis. According to an embodiment, the electronic device may generate a group with a similar activity amount patterns. For example, the electronic device may generate patterns including a similar characteristic vector as one group.

In operation 915, the electronic device (e.g., the activity pattern analysis module 230 shown in FIG. 2) may determine the distribution of an activity amount for each group. According to an embodiment, the electronic device may determine the distribution of an activity amount according to a time as an average value of an activity amount by using activity amount patterns thus grouped. As such, the electronic device may generate the statistical model 903 of an activity pattern on the specific time period by using the distribution of an activity amount determined as the average value.

According to various embodiments of the present disclosure, if a request is generated for each interval or in response to a user input, the electronic device may generate the probability of goal achievement 907 or the expected value of an activity amount 909 based on the collected activity information 905 and the statistical model of an activity pattern 903. For example, the electronic device may perform the function of a real-time processing on request 930.

According to the real-time processing on request 930, in operation 931, the electronic device (e.g., the activity pattern analysis module 230 shown in FIG. 2) may extract the characteristic of the activity information 905. According to an embodiment, the electronic device may extract the characteristic vector of the activity information 905. For example, the electronic device may distinguish the activity information 905 from an activity start time (e.g., 6 A.M.) to a specific time (e.g., a current time) during a specified time period (e.g., one day) as an activity amount according to a time and may extract a characteristic vector by connecting amounts of activities of a time when an activity amount rapidly increases.

In operation 933, the electronic device (e.g., the activity pattern analysis module 230 shown in FIG. 2) may determine the distribution of an activity amount. According to an embodiment, the electronic device may determine the distribution of an activity amount of the activity information 905 from the activity start time to the specific time. According to various embodiments of the present disclosure, when the electronic device determines the distribution of an activity amount, it may use the statistical model of an activity pattern 903. According to an embodiment, the electronic device may select an activity pattern, which is associated with a time period the same as or similar to the specified time period, from among patterns in the statistical model of an activity pattern 903. Furthermore, the electronic device may select one, which has time information similar to the activity start time or the specific time, from among patterns in the statistical model of an activity pattern 903. For example, the electronic device may select the statistical model 903 of an activity pattern in which at least one of a year, a month, a day, or a day of the week is the same as the activity start time or the specific time.

In operation 935, the electronic device (e.g., the activity pattern analysis module 230 shown in FIG. 2) may determine the probability of goal achievement 907. According to an embodiment, the electronic device may calculate the expected value of an activity amount 909 from the statistical model 903 of the selected activity pattern, may compare the expected value of an activity amount 909 with a specified activity goal, and may determine the probability of goal achievement 907 based on the compared result. According to an embodiment, the electronic device may calculate a ratio value of an activity goal amount, which is set to an activity goal, to a value obtained by summing an activity amount that is performed until a current time and the expected value of an activity amount 909. Also, the electronic device may assign the ratio value as the probability of goal achievement 907.

In operation 937, the electronic device (e.g., the activity pattern analysis module 230 shown in FIG. 2) may calculate the expected value of an activity amount 909. According to an embodiment, the electronic device may extract an activity amount, which corresponds to an activity after the specific time, from the statistical model 903 of an activity pattern. In addition, the electronic device may assign the extracted activity amount as the expected value of an activity amount 909. According to various embodiments of the present disclosure, the electronic device may extract an activity amount, which is performed until the specified time period ends, from the statistical model 903 of an activity pattern and may assign the extracted activity amount as the expected value of an activity amount 909. According to various embodiments, the electronic device may perform operation 935 after operation 937.

An electronic device and method according to an embodiment of the present disclosure may provide the information about activities in everyday life, which includes a movement amount and an exercise amount, thereby making it possible for a user to interactively operate the health management.

In addition, an electronic device and a method according to various embodiments of the present disclosure may determine the expected value of an activity amount, the probability that an activity goal is achieved, or the like based on the activity goal and an activity information and may provide the determined result, thereby adjusting an activity pace for achieving the activity goal of a user.

Furthermore, an electronic device and a method according to various embodiments of the present disclosure may notify a user of a proper activity based on the expected value of an activity amount and the probability that an activity goal is achieved, thereby increasing a probability that a user achieves the activity goal.

Figure 10:
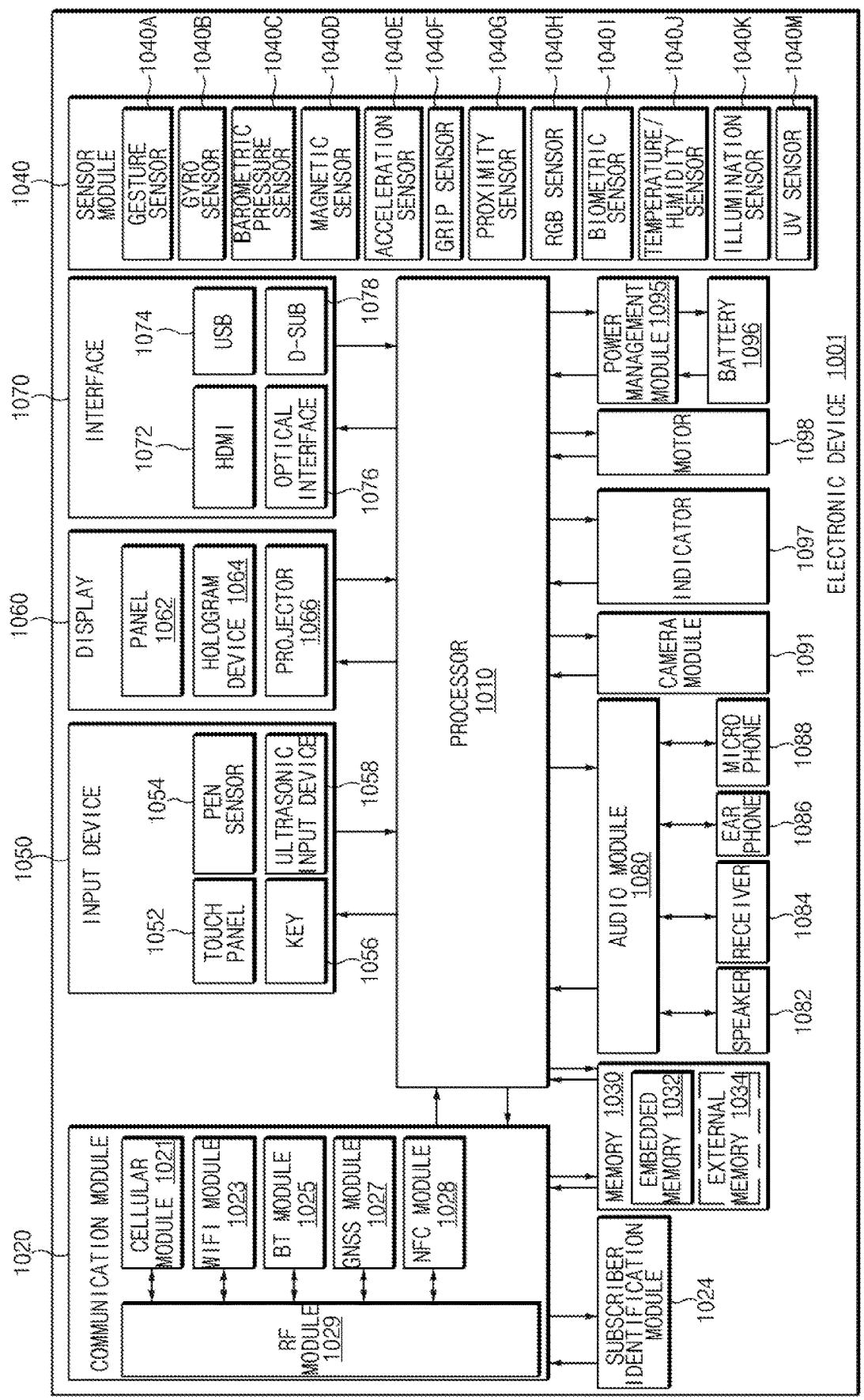
FIG. 10 is a block diagram illustrating an electronic device according to an embodiment of the present disclosure.

FIG. 10 is a block diagram illustrating an electronic device according to an embodiment of the present disclosure.

Referring to FIG. 10, an electronic device 1001 may include, for example, a part or the entirety of the electronic device 101 illustrated in FIG. 1A. The electronic device 1001 may include at least one processor (e.g., an AP) 1010, a communication module 1020, a subscriber identification module (SIM) 1024, a memory 1030, a sensor module 1040, an input device 1050, a display 1060, an interface 1070, an audio module 1080, a camera module 1091, a power management module 1095, a battery 1096, an indicator 1097, and a motor 1098.

The processor 1010 may run an operating system or an application program so as to control a plurality of hardware or software elements connected to the processor 1010, and may process various data and perform operations. The processor 1010 may be implemented with, for example, a system on chip (SoC). According to an embodiment of the present disclosure, the processor 1010 may further include a graphics processing unit (GPU) and/or an image signal processor. The processor 1010 may include at least a portion (e.g., a cellular module 1021) of the elements illustrated in FIG. 10. The processor 1010 may load, on a volatile memory, an instruction or data received from at least one of other elements (e.g., a nonvolatile memory) to process the instruction or data, and may store various data in a nonvolatile memory.

The communication module 1020 may have a configuration that is the same as or similar to that of the communication interface 170 shown in FIG. 1A. The communication module 1020 may include, for example, a cellular module 1021, a Wi-Fi module 1023, a Bluetooth (BT) module 1025, a GNSS module 1027 (e.g., a GPS module, a GLONASS module, a BeiDou module, or a Galileo module), a NFC module 1028, and a radio frequency (RF) module 1029.

The cellular module 1021 may provide, for example, a voice call service, a video call service, a text message service, or an Internet service through a communication network. The cellular module 1021 may identify and authenticate the electronic device 1001 in the communication network using the subscriber identification module 1024 (e.g., a SIM card). The cellular module 1021 may perform at least a part of functions that may be provided by the processor 1010. The cellular module 1021 may include a communication processor (CP).

Each of the Wi-Fi module 1023, the BT module 1025, the GNSS module 1027 and the NFC module 1028 may include, for example, a processor for processing data transmitted/received through the modules. According to some various embodiments of the present disclosure, at least a part (e.g., two or more) of the cellular module 1021, the Wi-Fi module 1023, the BT module 1025, the GNSS module 1027, and the NFC module 1028 may be included in a single integrated chip (IC) or IC package.

The RF module 1029 may transmit/receive, for example, communication signals (e.g., RF signals). The RF module 1029 may include, for example, a transceiver, a power amp module (PAM), a frequency filter, a low noise amplifier (LNA), an antenna, or the like. According to another embodiment of the present disclosure, at least one of the cellular module 1021, the Wi-Fi module 1023, the BT module 1025, the GNSS module 1027, or the NFC module 1028 may transmit/receive RF signals through a separate RF module.

The SIM 1024 may include, for example, an embedded SIM and/or a card containing the subscriber identity module, and may include unique identification information (e.g., an integrated circuit card identifier (ICCID)) or subscriber information (e.g., international mobile subscriber identity (IMSI)).

The memory 1030 (e.g., the memory 130) may include, for example, an internal memory 1032 or an external memory 1034. The internal or embedded memory 1032 may include at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, a NOR flash memory, or the like)), a hard drive, or a solid state drive (SSD).

The external memory 1034 may include a flash drive such as a compact flash (CF), a secure digital (SD), a micro-SD, a mini-SD, an extreme digital (xD), a multimedia card (MMC), a memory stick, or the like. The external memory 1034 may be operatively and/or physically connected to the electronic device 1001 through various interfaces.

The sensor module 1040 may, for example, measure physical quantity or detect an operation state of the electronic device 1001 so as to convert measured or detected information into an electrical signal. The sensor module 1040 may include, for example, at least one of a gesture sensor 1040A, a gyro sensor 1040B, a barometric pressure sensor 1040C, a magnetic sensor 1040D, an acceleration sensor 1040E, a grip sensor 1040F, a proximity sensor 1040G, a color sensor 1040H (e.g., a red/green/blue (RGB) sensor), a biometric sensor 1040I, a temperature/humidity sensor 1040J, an illumination sensor 1040K, or an ultraviolet (UV) sensor 1040M. Additionally or alternatively, the sensor module 1040 may include, for example, an olfactory sensor such as an electric nose (E-nose) sensor, an electromyography (EMG) sensor, an electroencephalogram (EEG) sensor, an electrocardiogram (ECG) sensor, an infrared (IR) sensor, an iris recognition sensor, and/or a fingerprint sensor. The sensor module 1040 may further include a control circuit for controlling at least one sensor included therein. In some various embodiments of the present disclosure, the electronic device 1001 may further include a processor configured to control the sensor module 1040 as a part of the processor 1010 or separately, so that the sensor module 1040 is controlled while the processor 1010 is in a sleep state.

The input device 1050 may include, for example, a touch panel 1052, a digital stylus or (digital) pen sensor 1054, a key 1056, or an ultrasonic input device 1058. The touch panel 1052 may employ at least one of capacitive, resistive, infrared, and ultraviolet sensing methods. The touch panel 1052 may further include a control circuit. The touch panel 1052 may further include a tactile layer so as to provide a haptic feedback to a user.

The digital stylus or (digital) pen sensor 1054 may include, for example, a sheet for recognition which is a part of a touch panel or is separate. The key 1056 may include, for example, a physical button, an optical button, or a keypad. The ultrasonic input device 1058 may sense ultrasonic waves generated by an input tool through a microphone 1088 so as to identify data corresponding to the ultrasonic waves sensed.

The display 1060 (e.g., the display 160 shown in FIG. 1A) may include a panel 1062, a hologram device 1064, or a projector 1066. The panel 1062 may have a configuration that is the same as or similar to that of the display 160 shown in FIG. 1A. The panel 1062 may be, for example, flexible, transparent, or wearable. The panel 1062 and the touch panel 1052 may be integrated into a single module. The hologram device 1064 may display a stereoscopic image in a space using a light interference phenomenon. The projector 1066 may project light onto a screen so as to display an image. The screen may be disposed in the inside or the outside of the electronic device 1001. According to an embodiment of the present disclosure, the display 1060 may further include a control circuit for controlling the panel 1062, the hologram device 1064, or the projector 1066.

The interface 1070 may include, for example, an HDMI 1072, a USB 1074, an optical interface 1076, or a D-sub-miniature (D-sub) 1078. The interface 1070, for example, may be included in the communication interface 170 illustrated in FIG. 1A. Additionally or alternatively, the interface 1070 may include, for example, a mobile high-definition link (MHL) interface, an SD card/multi-media card (MMC) interface, or an infrared data association (IrDA) interface.

The audio module 1080 may convert, for example, a sound into an electrical signal or vice versa. At least a portion of elements of the audio module 1080 may be included in the input/output interface 150 illustrated in FIG. 1A. The audio module 1080 may process sound information input or output through a speaker 1082, a receiver 1084, an earphone 1086, or the microphone 1088.

The camera module 1091 is, for example, a device for shooting a still image or a video. According to an embodiment of the present disclosure, the camera module 1091 may include at least one image sensor (e.g., a front sensor or a rear sensor), a lens, an image signal processor (ISP), or a flash (e.g., an LED or a xenon lamp).

The power management module 1095 may manage power of the electronic device 1001. According to an embodiment of the present disclosure, the power management module 1095 may include a power management integrated circuit (PMIC), a charger integrated circuit (IC), or a battery or gauge. The PMIC may employ a wired and/or wireless charging method. The wireless charging method may include, for example, a magnetic resonance method, a magnetic induction method, an electromagnetic method, or the like. An additional circuit for wireless charging, such as a coil loop, a resonant circuit, a rectifier, or the like, may be further included. The battery gauge may measure, for example, a remaining capacity of the battery 1096 and a voltage, current or temperature thereof while the battery is charged. The battery 1096 may include, for example, a rechargeable battery and/or a solar battery.

The indicator 1097 may display a specific state of the electronic device 1001 or a part thereof (e.g., the processor 1010), such as a booting state, a message state, a charging state, or the like. The motor 1098 may convert an electrical signal into a mechanical vibration, and may generate a vibration or haptic effect. Although not illustrated, a processing device (e.g., a GPU) for supporting a mobile TV may be included in the electronic device 1001. The processing device for supporting a mobile TV may process media data according to the standards of digital multimedia broadcasting (DMB), digital video broadcasting (DVB), MediaFLO™, or the like.

Each of the elements described herein may be configured with one or more components, and the names of the elements may be changed according to the type of an electronic device. In various embodiments of the present disclosure, an electronic device may include at least one of the elements described herein, and some elements may be omitted or other additional elements may be added. Furthermore, some of the elements of the electronic device may be combined with each other so as to form one entity, so that the functions of the elements may be performed in the same manner as before the combination.

Figure 11:
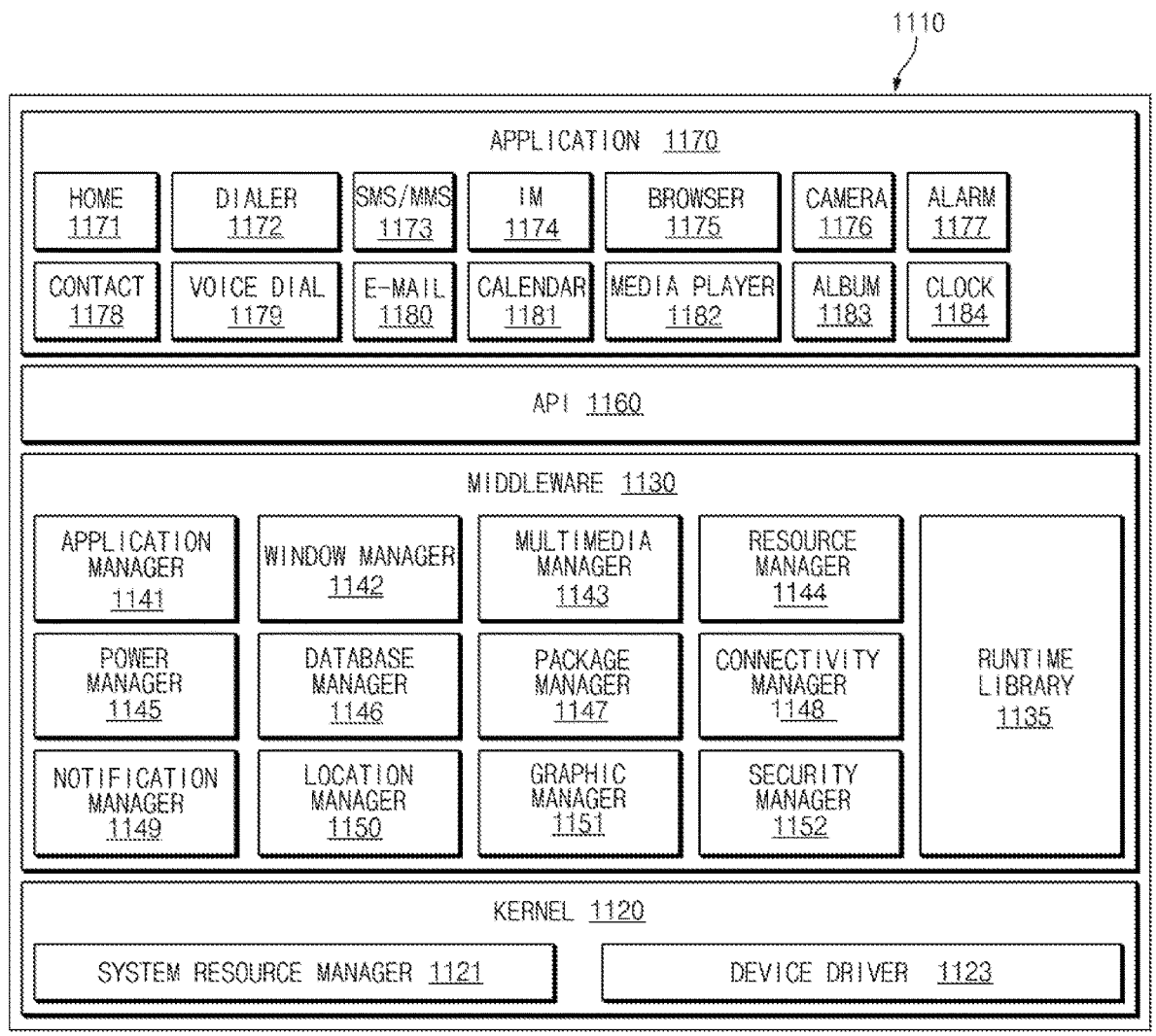
FIG. 11 is a block diagram illustrating a program module according to an embodiment of the present disclosure.

FIG. 11 is a block diagram illustrating a program module according to an embodiment of the present disclosure.

Referring to FIG. 11, a program module 1110 (e.g., the program 140 shown in FIG. 1A) may include an operating system (OS) for controlling a resource related to an electronic device (e.g., the electronic device 101 shown in FIG. 1A) and/or various applications (e.g., the application program 147 shown in FIG. 1A) running on the OS. The operating system may be, for example, Android™, iOS™, Windows™, Symbian®, Tizen®, Bada® or the like.

The program module 1110 may include a kernel 1120, a middleware 1130, an API 1160, and/or an application 1170. At least a part of the program module 1110 may be preloaded on an electronic device or may be downloaded from an external electronic device (e.g., the first electronic device 102, the second external electronic device 104, or the server 106, shown in FIG. 1A).

The kernel 1120 (e.g., the kernel 141) may include, for example, a system resource manager 1121 or a device driver 1123. The system resource manager 1121 may perform control, allocation, or retrieval of a system resource. According to an embodiment of the present disclosure, the system resource manager 1121 may include a process management unit, a memory management unit, a file system management unit, or the like. The device driver 1123 may include, for example, a display driver, a camera driver, a Bluetooth driver, a shared memory driver, a USB driver, a keypad driver, a Wi-Fi driver, an audio driver, or an inter-process communication (IPC) driver.

The middleware 1130, for example, may provide a function that the applications 1170 require in common, or may provide various functions to the applications 1170 through the API 1160 so that the applications 1170 may efficiently use limited system resources in the electronic device. According to an embodiment of the present disclosure, the middleware 1130 (e.g., the middleware 143 shown in FIG. 1) may include at least one of a runtime library 1135, an application manager 1141, a window manager 1142, a multimedia manager 1143, a resource manager 1144, a power manager 1145, a database manager 1146, a package manager 1147, a connectivity manager 1148, a notification manager 1149, a location manager 1150, a graphic manager 1151, and a security manager 1152.

The runtime library 1135 may include, for example, a library module that a complier uses to add a new function through a programming language while the application 1170 is running. The runtime library 1135 may perform a function for input/output management, memory management, or an arithmetic function.

The application manager 1141 may mange, for example, a life cycle of at least one of the applications 1170. The window manager 1142 may manage a graphical user interface (GUI) resource used in a screen. The multimedia manager 1143 may recognize a format required for playing various media files and may encode or decode a media file using a codec matched to the format. The resource manager 1144 may manage a resource such as a source code, a memory, or a storage space of at least one of the applications 1170.

The power manager 1145, for example, may operate together with a basic input/output system (BIOS) to manage a battery or power and may provide power information required for operating the electronic device. The database manager 1146 may generate, search, or modify a database to be used in at least one of the applications 1170. The package manager 1147 may manage installation or update of an application distributed in a package file format.

The connectivity manger 1148 may manage wireless connection of Wi-Fi, Bluetooth, or the like. The notification manager 1149 may display or notify an event such as message arrival, appointments, and proximity alerts in such a manner as not to disturb a user. The location manager 1150 may manage location information of the electronic device. The graphic manager 1151 may manage a graphic effect to be provided to a user or a user interface related thereto. The security manager 1152 may provide various security functions required for system security or user authentication. According to an embodiment of the present disclosure, in the case in which an electronic device (e.g., the electronic device 101 shown in FIG. 1A) includes a phone function, the middleware 1130 may further include a telephony manager for managing a voice or video call function of the electronic device.

The middleware 1130 may include a middleware module for forming a combination of various functions of the above-mentioned elements. The middleware 1130 may provide a module specialized for each type of an operating system to provide differentiated functions. Furthermore, the middleware 1130 may delete a part of existing elements or may add new elements dynamically.

The API 1160 (e.g., the API 145 shown in FIG. 1A) which is, for example, a set of API programming functions may be provided in different configurations according to an operating system. For example, in the case of Android™ or iOS™, one API set may be provided for each platform, and, in the case of Tizen®, at least two API sets may be provided for each platform.

The application 1170 (e.g., the application program 147 shown in FIG. 1A), for example, may include at least one application capable of performing functions such as a home 1171, a dialer 1172, a short message service (SMS)/multimedia message service (MMS) 1173, an instant message (IM) 1174, a browser 1175, a camera 1176, an alarm 1177, a contact 1178, a voice dial 1179, an e-mail 1180, a calendar 1181, a media player 1182, an album 1183, a clock 1184, health care (e.g., measure an exercise amount or blood sugar), or environmental information provision (e.g., provide air pressure, humidity, or temperature information).

According to an embodiment of the present disclosure, the application 1170 may include an information exchange application for supporting information exchange between the electronic device (e.g., the electronic device 101 shown in FIG. 1A) and an external electronic device (e.g., the first electronic device 102 or the second external electronic device 104, shown in FIG. 1A). The information exchange application may include, for example, a notification relay application for relaying specific information to the external electronic device or a device management application for managing the external electronic device.

For example, the notification relay application may have a function for relaying, to an external electronic device (e.g., the first electronic device 102 or the second external electronic device 104, shown in FIG. 1A), notification information generated in another application (e.g., an SMS/MMS application, an e-mail application, a health care application, an environmental information application, or the like) of the electronic device. Furthermore, the notification relay application may receive notification information from the external electronic device and may provide the received notification information to the user.

The device management application, for example, may manage (e.g., install, delete, or update) at least one function (e.g., turn-on/turn off of the external electronic device itself (or some elements) or the brightness (or resolution) adjustment of a display) of the external electronic device (e.g., the first electronic device 102 or the second external electronic device 104, shown in FIG. 1A) communicating with the electronic device, an application running in the external electronic device, or a service (e.g., a call service, a message service, or the like) provided from the external electronic device.

According to an embodiment of the present disclosure, the application 1170 may include a specified application (e.g., a healthcare application of a mobile medical device) according to an attribute of the external electronic device (e.g., the first electronic device 102 or the second external electronic device 104). The application 1170 may include an application received from an external electronic device (e.g., the first electronic device 102 or the second external electronic device 104). The application 1170 may include a preloaded application or a third-party application downloadable from a server. The names of the elements of the program module 1110 illustrated may vary with the type of an operating system.

According to various embodiments of the present disclosure, at least a part of the program module 1110 may be implemented with software, firmware, hardware, or a combination thereof. At least a part of the program module 1110, for example, may be implemented (e.g., executed) by a processor (e.g., the processor 1010). At least a part of the program module 1110 may include, for example, a module, a program, a routine, sets of instructions, or a process for performing at least one function.

The term "module" used herein may represent, for example, a unit including one of hardware, software and firmware or a combination thereof. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. For example, the "module" may include at least one of an application-specific integrated circuit (ASIC) chip, a field-programmable gate array (FPGA), and a programmable-logic device for performing some operations, which are known or will be developed.

At least a part of devices (e.g., modules or functions thereof) or methods (e.g., operations) according to various embodiments of the present disclosure may be implemented as instructions stored in a computer-readable storage medium in the form of a program module. In the case where the instructions are performed by a processor (e.g., the processor 120 shown in FIG. 1A), the processor may perform functions corresponding to the instructions. The computer-readable storage medium may be, for example, the memory 130 (shown in FIG. 1A).

A computer-readable recording medium may include a hard disk, a floppy disk, a magnetic medium (e.g., a magnetic tape), an optical medium (e.g., compact disc ROM (CD-ROM), DVD), a magneto-optical medium (e.g., a floptical disk), or a hardware device (e.g., a ROM, a RAM, a flash memory, or the like). The program instructions may include machine language codes generated by compilers and high-level language codes that can be executed by computers using interpreters. The above-mentioned hardware device may be configured to be operated as one or more software modules for performing operations of various embodiments of the present disclosure and vice versa.

For example, an electronic device may include a processor and a memory for storing computer-readable instructions. The memory may include instructions for performing the above-mentioned various methods or functions when executed by the processor. For example, the memory may include instructions that, when executed by the processor, cause the processor to execute collecting sensing information according to a motion of an electronic device, obtaining activity information comprising at least one of an exercise amount that is calculated based on first sensing information obtained according to execution of a specified workout, and a movement amount that is calculated based on second sensing information obtained according to a daily life, determining an expected value of an activity amount, by which a user works out, during a specific time period by a user, based on the activity information, and providing guide information for achieving an activity goal associated with the user based on at least one of the expected value of the activity amount and the activity information.

A module or a program module according to various embodiments of the present disclosure may include at least one of the above-mentioned elements, or some elements may be omitted or other additional elements may be added. Operations performed by the module, the program module or other elements according to various embodiments of the present disclosure may be performed in a sequential, parallel, iterative or heuristic way. Furthermore, some operations may be performed in another order or may be omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A portable electronic device comprising:
a sensor configured to collect sensing information, the sensing information including information according to a motion of the portable electronic device and biometric information of a user; and
at least one processor operatively connected with the sensor,
wherein the at least one processor is configured to control for:
obtaining activity information including at least one of an exercise amount that is calculated based on first sensing information obtained according to execution of a specified workout, or a movement amount that is calculated based on second sensing information obtained according to a daily life, determining an expected value of an activity amount, by which the user works out, during a specific time period by the user based on the activity information, determining a probability of achievement with respect to an activity goal associated with the user based on the expected value of the activity amount, providing guide information for achieving the activity goal associated with the user based on at least one of the expected value of the activity amount or the activity information, and providing a feedback on the activity information based on the expected value of the activity amount, the feedback including one of a visual or audio effect, wherein the guide information indicates a recommendation to maintain a current activity when the probability of achievement is greater than or equal to a threshold, wherein the guide information indicates a recommendation to perform another activity having an intensity higher than an intensity of the current activity when the probability of achievement is less than the threshold, wherein when the probability of achievement is greater than or equal to the threshold, an activity guide screen including a recommended activity displaying object is output, and wherein the recommended activity displaying object includes information of a kind of activity, an activity amount per time according to each activity, and a recommended activity time.

2. The portable electronic device of claim 1, wherein the at least one processor is further configured to control for analyzing an activity pattern of the user based on the activity information.

3. The portable electronic device of claim 2, wherein the at least one processor is further configured to control for determining the expected value of the activity amount based on the activity pattern.

4. The portable electronic device of claim 3, wherein the at least one processor is further configured to control for providing a notification on the probability of achievement.

5. The portable electronic device of claim 4, wherein the at least one processor is further configured to control for providing information about the activity pattern together when the notification on the probability of achievement is provided.

6. The portable electronic device of claim 1, wherein the at least one processor is further configured to control for providing the feedback by using a visual effect corresponding to at least one of the activity goal, the activity information, or the expected value of the activity amount.

7. The portable electronic device of claim 1, wherein the guide information further comprises guide information about a second activity different from a first activity associated with the activity goal.

8. The portable electronic device of claim 7, wherein the guide information about the second activity comprises at least one of a kind of the second activity, an activity amount per time of the second activity, a recommended activity time of the second activity, recommended activity intensity of the second activity, or an execution schedule of the second activity.

9. The portable electronic device of claim 1, wherein the at least one processor is further configured to control for providing the guide information to an external electronic device connected through a communication interface.

10. A method comprising:

collecting sensing information, the sensing information including information according to a motion of a portable electronic device and biometric information of a user;

obtaining activity information comprising at least one of an exercise amount that is calculated based on first sensing information obtained according to execution of a specified workout, or a movement amount that is calculated based on second sensing information obtained according to a daily life;

determining an expected value of an activity amount, by which the user works out, during a specific time period by a user, based on the activity information;

determining a probability of achievement with respect to an activity goal associated with the user based on the expected value of the activity amount;

providing guide information for achieving the activity goal associated with the user based on at least one of the expected value of the activity amount or the activity information; and providing a feedback on the activity information based on the expected value of the activity amount, the feedback comprising one of a visual or audio effect, wherein the guide information indicates a recommendation to maintain a current activity when the probability of achievement is greater than or equal to a threshold, wherein the guide information indicates a recommendation to perform another activity having an intensity higher than an intensity of the current activity when the probability of achievement is less than the threshold, wherein when the probability of achievement is greater than or equal to the threshold, an activity guide screen including a recommended activity displaying object is output, and wherein the recommended activity displaying object includes information of a kind of activity, an activity amount per time according to each activity, and a recommended activity time.

11. The method of claim 10, further comprising:

analyzing an activity pattern of the user based on the activity information.

12. The method of claim 11, wherein the determining of the expected value of the activity amount comprises:

determining the expected value of the activity amount based on the activity pattern.

13. The method of claim 12, further comprising:

providing a notification on the probability of achievement.

14. The method of claim 13, wherein the providing of the notification further comprises:

providing information about the activity pattern.

15. The method of claim 10, wherein the providing of the guide information further comprises:

providing guide information about a second activity different from a first activity associated with the activity goal.

16. The method of claim 15, wherein the providing of the guide information about the second activity comprises:

providing at least one of a kind of the second activity, an activity amount per time of the second activity, a recommended activity time of the second activity, recommended activity intensity of the second activity, or an execution schedule of the second activity.

17. The method of claim 10, wherein the providing of the guide information further comprises:

provided the guide information to an external electronic device connected through a communication interface.

18. A non-transitory computer-readable recording medium having recorded thereon at least one program comprising commands which, when executed by at least one processor, performs a method, the method comprising:

collecting sensing information, the sensing information including information according to a motion of a portable electronic device and biometric information of a user, obtaining activity information comprising at least one of an exercise amount that is calculated based on first sensing information obtained according to execution of a specified workout, or a movement amount that is calculated based on second sensing information obtained according to a daily life, determining an expected value of an activity amount, by which a user works out, during a specific time period by a user, based on the activity information, determining a probability of achievement with respect to an activity goal associated with the user based on the expected value of the activity amount, providing guide information for achieving the activity goal associated with the user based on at least one of the expected value of the activity amount or the activity information, and providing a feedback on the activity information based on the expected value of the activity amount, the feedback comprising one of a visual or audio effect, wherein the guide information indicates a recommendation to maintain a current activity when the probability of achievement is greater than or equal to a threshold, wherein the guide information indicates a recommendation to perform another activity having an intensity higher than an intensity of the current activity when the probability of achievement is less than the threshold, wherein when the probability of achievement is greater than or equal to the threshold, an activity guide screen including a recommended activity displaying object is output, and wherein the recommended activity displaying object includes information of a kind of activity, an activity amount per time according to each activity, and a recommended activity time.

\* \* \* \* \*